United States Patent [19]

Collins et al.

[11] Patent Number: 4,818,680

[45] Date of Patent: Apr. 4, 1989

[54] METHOD AND KIT INVOLVING DISPLACEMENT AND REHYBRIDIZATION OF LABELED POLYNUCLEOTIDE

[76] Inventors: Mary Collins, 27 Euclid Ave., Natick, Mass. 01760; Joseph P. Dougherty, 123 Highland Ave., Somerville, Mass. 02143; Marian S. Ellwood, R.D. 4, Box 109, Lebanon, N.J. 08833; Edward F. Fritsch, 115 North Branch Rd., Concord, Mass. 01742; Kenneth A. Jacobs, 151 Beaumont Ave., Newton, Mass. 02160

[21] Appl. No.: 811,034

[22] Filed: Dec. 18, 1985

[51] Int. Cl.[4] .................. C12Q 1/68; C12N 33/53; G01N 33/566

[52] U.S. Cl. ........................... 435/6; 435/7; 435/810; 436/501; 935/77; 935/78; 536/26; 536/27; 536/28

[58] Field of Search ............... 435/6, 7, 810; 436/501; 935/77, 78; 536/27, 28, 26

[56] References Cited

U.S. PATENT DOCUMENTS 4,205,952  6/1980  Cais .................................. 436/801 X
4,563,417  1/1986  Albarella et al. ................. 935/77 X

FOREIGN PATENT DOCUMENTS 0139489  5/1985  European Pat. Off. ............... 435/6
2139349  11/1984  United Kingdom .

Primary Examiner—Robert J. Warden
Assistant Examiner—Jack Spiegel
Attorney, Agent, or Firm—Richard C. Stewart, II; Gerhard Fuchs

[57] ABSTRACT

A diagnostic reagent is disclosed which is capable of binding to a target nucleotide sequence which is bound to a labeled polynucleotide in a target binding region which is at least partially co-extensive with the target binding region in the probe polynucleotide which is capable of binding to the target nucleotide sequence. A method is disclosed in which the reagent is contacted with a sample and with a capturing polynucleotide under conditions such that target nucleotide which may be present in the sample binds to the probe polynucleotide and displaces labeled polynucleotide from the reagent complex, and the capturing polynucleotide binds selectively to the displaced labeled polynucleotide in the region of the labeled polynucleotide that had been bound to the probe polynucleotide. Determination of the displaced nucleotide gives a value which is a function of the presence and concentration of target nucleotide in the sample.

43 Claims, 4 Drawing Sheets

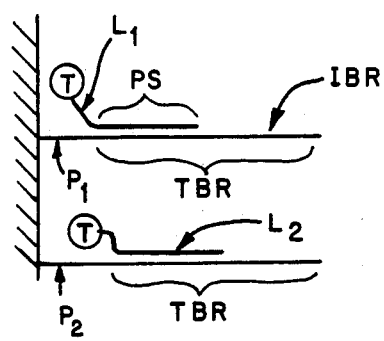
FIG. 1A
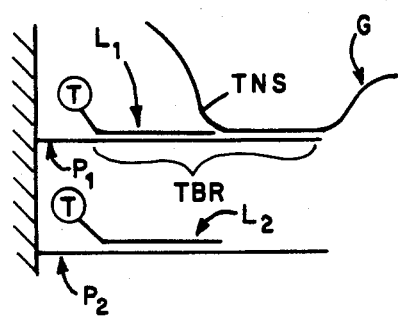
FIG. 1B
FIG. 1C
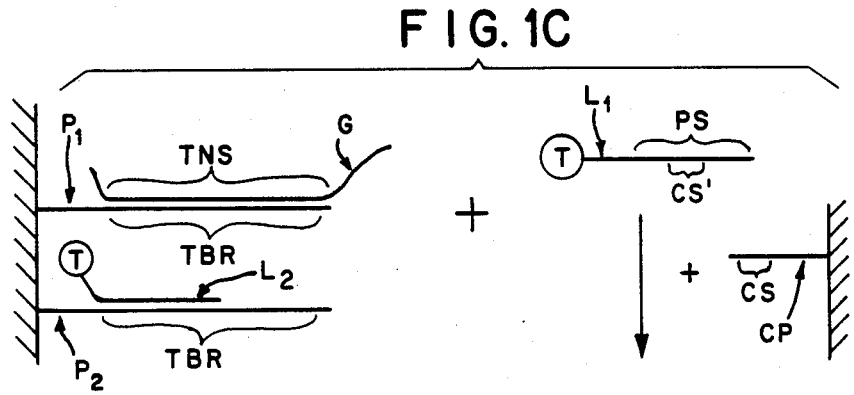
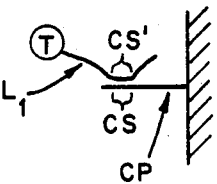
FIG. 1D

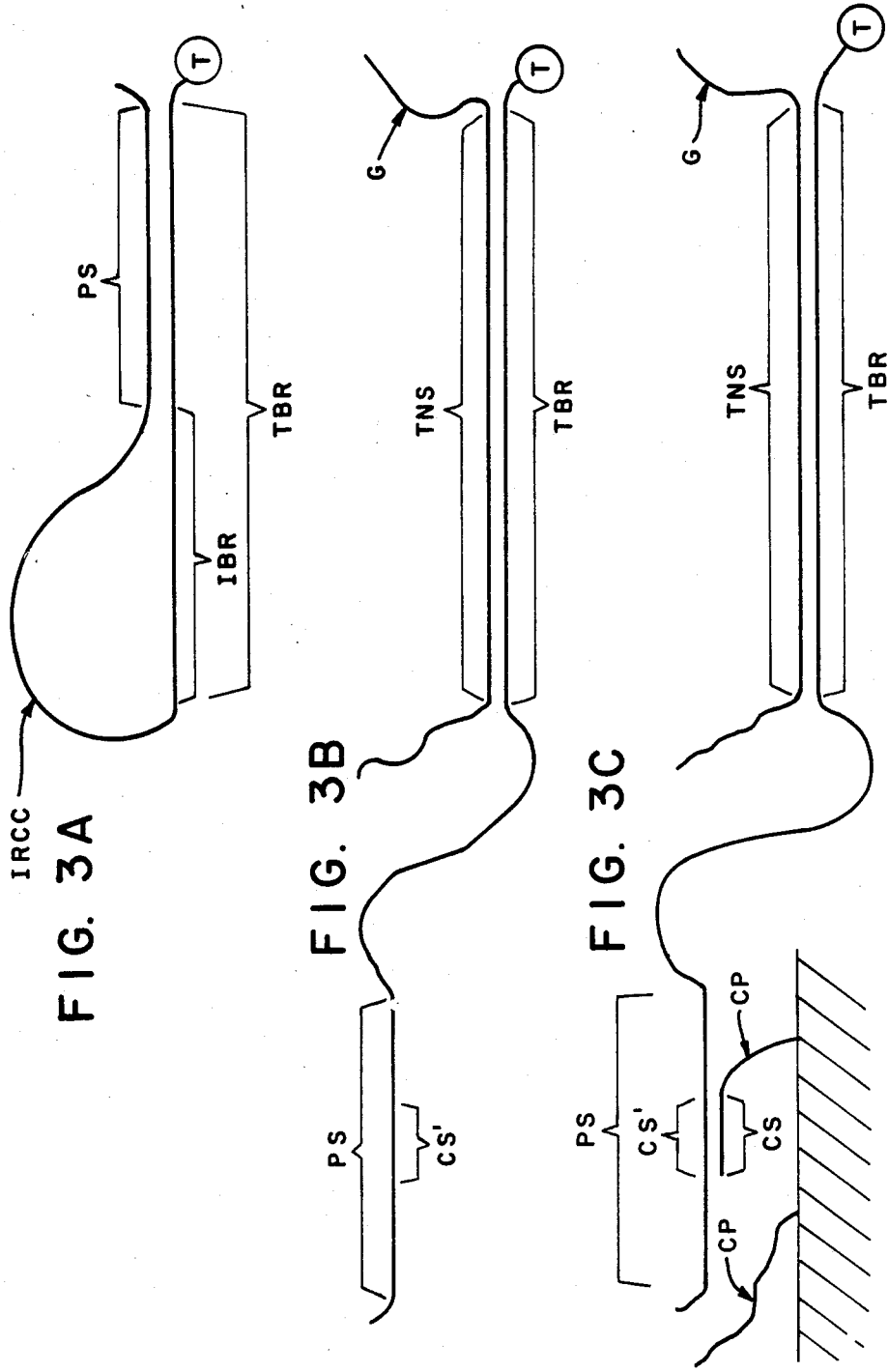

FIG. 4
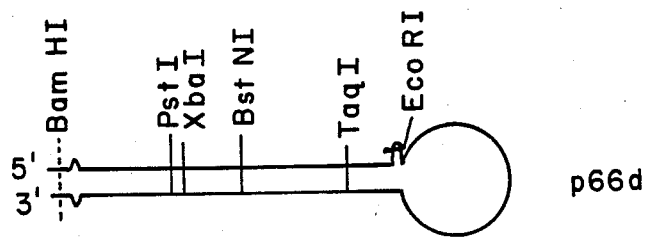
p66d
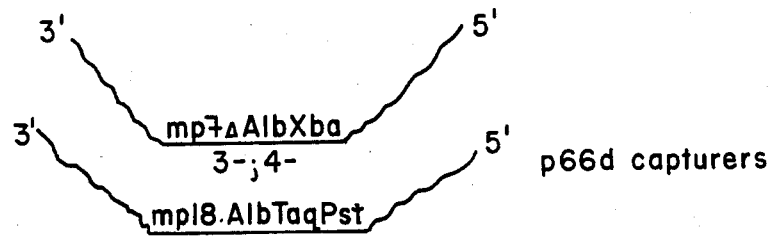
p66d capturers
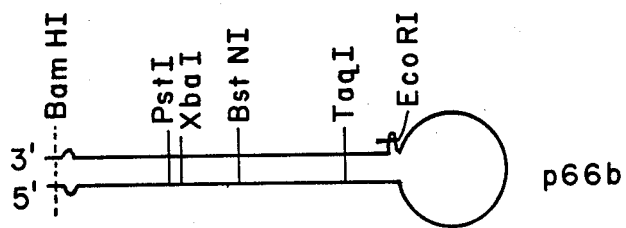
p66b
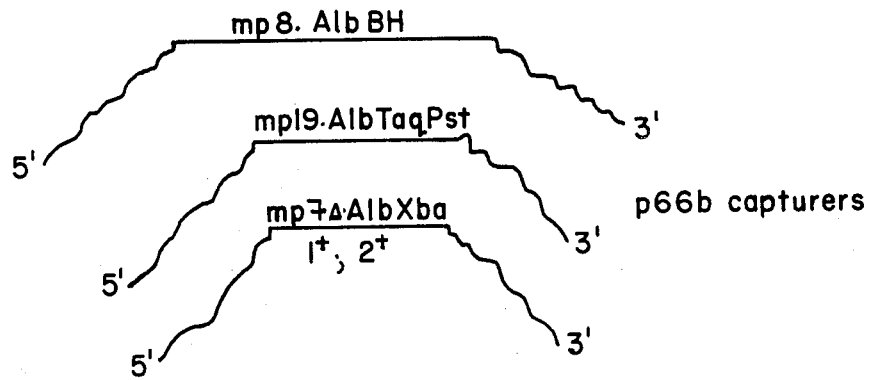
p66b capturers

METHOD AND KIT INVOLVING DISPLACEMENT AND REHYBRIDIZATION OF LABELED POLYNUCLEOTIDE

BACKGROUND OF THE INVENTION

The present invention relates to methods for the determination of target nucleotide sequences, and to diagnostic kits suitable for such methods.

A group of inventors, including some of the present inventors, have disclosed in U.S Ser. No. 607,885, and in several further patent applications discussed below, a nucleic acid assay based upon strand displacement. Such assay employs a reagent complex of:

(a) a probe polynucleotide (P) having a target binding region (TBR) complementary to the target nucleotide sequence (TNS) to be detected, and (b) a labeled polynucleotide (L) (or signal strand) bound in the reagent complex to the probe polynucleotide (P) in at least a portion of the target binding region (TBR).

The portion of the labeled polynucleotide (L) so-bound is sometimes referred to in those applications as the pairing segment (PS). In the assay, the target nucleotide sequence (TNS) binds to the target binding region (TBR) and displaces the labeled polynucleotide (L). The displaced labeled polynucleotide is then detected as a measure of the presence and amount of target nucleotide sequence (TNS) in the sample.

In those patent applications, separation of displaced labeled polynucleotides from intact reagent complexes is described for many forms of the invention. Two forms of separation involve: (a) a reagent complex in which the probe polynucleotide is immobilized and (b) a reagent complex in which the probe polynucleotide is in solution with a pendant affinity moiety (e.g., biotin) for post-displacement immobilization. In U.S Ser. No. 729,501 of Unger, et al. various other groups in or of the probe (e.g., a poly-dC tail) are disclosed for post-displacement immobilization. In such cases of immobilized probes or post-displacement immobilization of the probe, the displaced labeled polynucleotides remain in solution for detection. In the usual event, only a small proportion (1% to 0.00001%) of labeled polynucleotides are displaced, however, a variety of mechanisms such as strand breakage of regent complexes detachment of immobilized reagent complexes from the solid or inefficient trapping of immobilizable complexes, can result in labeled polynucleotides remaining in solution in the absence of specific displacement events. These mechanisms are a source of background for the assay. The level of tolerable background will depend upon both the number of reagent complexes used in the reaction and the amount of analyte to be detected. For example, to detect $10^6$ analytes in a reaction with $10^{11}$ reagent complexes, 0.001% ($10^6$) or fewer complexes must be released or not immobilized as background for any signal to be detected with a (signal & background)/background ratio of at least 2/1.

In U.S. Ser. No. 607,885, embodiments are shown (e.g., in FIG. 2A) wherein the labeled polynucleotide L bears an affinity moiety (biotin) for post-displacement immobilization. While such technique concentrates the signal (a desirable result in many cases), it is unlikely to aid in background reduction, since displaced labeled polynucleotides and detached reagent complexes each have biotin and are likely to be immobilized with substantially equal efficiency.

Other pending U.S. patent applications concerned with strand displacement of nucleic acids include the following:

| | | |
|---|---|---|
| 684,305 | December 10, 1984 | Collins, et al. |
| 684,308 | December 10, 1984 | Williams, et al. |
| 729,501 | May 2, 1985 | Unger, et al. |
| 729,503 | May 2, 1985 | Vary, et al. |
| 729,504 | May 2, 1985 | Fritsch, et al. |
| 777,796 | September 19, 1985 | Fritsch, et al. |

In addition; U.S Ser. No. 790,671 of Ellwood, et al, discussed more fully below, relates to an assay involving hybridization, but not strand displacement.

BRIEF DESCRIPTION OF THE INVENTION

The present invention provides a first method for determining the presence or amount of a predetermined target nucleotide sequence in the nucleic acid of a biological sample which comprises the steps:

(a) providing a reagent complex of (i) a probe polynucleotide which is capable of complementary base pair binding to the target nucleotide sequence, and (ii) a labeled polynucleotide which is bound by complementary base pair binding to the probe polynucleotide in a region of the probe polynucleotide at least partially coextensive with the region in which the probe polynucleotide is capable of binding to the target nucleotide sequence;

(b) contacting the reagent complex with a sample and with a capturing polynucleotide under conditions in which the target nucleotide sequence, if present, binds to the probe polynucleotide and displaces labeled polynucleotide from the reagent complex, and in which the capturing polynucleotide binds by complementary base pair binding selectively to the displaced labeled polynucleotide in a region of the labeled polynucleotide that had been bound to the probe polynucleotide by complementary base pair binding, (c) separating displaced labeled polynucleotide which has bound to capturing polynucleotide from labeled polynucleotide which has not bound to capturing polynucleotide, and (d) detecting displaced labeled polynucleotide which has bound to capturing polynucleotide and has been separated.

The present invention further provides a first kit for determining the presence of a predetermined target nucleotide sequence in the nucleic acid of a biological sample which comprises:

(a) a reagent complex of:

(i) a probe polynucleotide which is capable of complementary base pair binding to the target nucleotide sequence, and (ii) a labeled polynucleotide which is bound by complementary base pair binding of a first binding region of the labeled polynucleotide to a labeled polynucleotide binding region of the probe polynucleotide, which labeled polynucleotide binding region is at least partially coextensive with the region in which the probe polynucleotide is capable of binding to the target nucleotide sequence;

(b) a capture polynucleotide having a second binding region capable of complementary base pair binding selectively to a segment of displaced labeled polynucleotide substantially within the first binding region, and (c) means for isolating the capture polynucleotide together with any attached displaced labeled polynucleotide from intact reagent complex.

Such first method and kit are particularly adapted to reduce background label detection in those instances of the previously disclosed displacement assays where: (1) the proportion of displaced labeled polynucleotide relative to intact reagent complexes is low, and (2) an amount of background label detection is attributable to detached reagent complexes, cleaved reagent complexes and/or intact reagent complexes not immobilized in a post-displacement immobilization step. Such method and kit are further particularly adapted to certain embodiments of strand displacement in solution wherein the present capturing polynucleotide is the sole or primary means for separating displaced labeled polynucleotides from intact reagent complexes.

The present invention further provides a similar method and kit applicable to the inverse reagent complex and inverse displacement assay method of copending application Ser. No. 809,992 of M. Collins et. al., filed herewith. In such cases, it is the labeled probe polynucleotide which contains the detectable tag, but the target nucleotide sequence is fully-bound to target binding region in the displaced strands to be detected. Accordingly, the present invention is applicable only if the labeled probe polynucleotide is covalently bound to a pairing segment which has been displaced from the target binding region by the target nucleotide sequence (see FIGS. 3A-3C).

Thus the present invention further includes a method and kit for determining the presence or amount of a predetermined target nucleotide sequence in the nucleic acid of a biological sample. The method comprises the steps:

(a) providing a reagent complex construct which comprises (1) a stably joined polynucleotide having: (i) a target binding region segment which is capable of complementary base pair binding to the target nucleotide sequence and (ii) a pairing segment which is bound by complementary base pair binding to a portion of the target binding region segment, and (2) a detectable tag which is in or adjacent to the target binding region segment;

(b) contacting the sample with the reagent complex construct and with a capture polynucleotide under conditions in which the target nucleotide sequence displaces pairing segment from target binding region segment, and in which the capture polynucleotide binds by complementary base pair binding selectively to the displaced pairing segment;

(c) separating polynucleotides which have bound to capture polynucleotides from polynucleotides which have not bound to capture polynucleotides; and (d) detecting the detectable tag which is on polynucleotides which have bound to capture polynucleotides and have been separated.

The kit comprises:

(a) a reagent complex construct which comprises (1) a polynucleotide (including two or more stably joined polynucleotides) having: (i) a target binding region segment which is capable of complementary base pair binding to the target nucleotide sequence and (ii) a pairing segment which is bound by complementary base pair binding to a portion of the target binding region segment, and (2) a detectable tag adjacent to the target binding region segment;

(b) a capture polynucleotide capable of complementary base pair binding to the pairing segment selectively when the pairing segment is displaced from the target binding region segment; and (c) means for separating capture polynucleotide, together with attached polynucleotide strand, from reagent complex constructs in which the pairing segment remains bound by complementary base pair binding to the target binding region segment.

DETAILED DESCRIPTION OF THE INVENTION

Figure 2A:
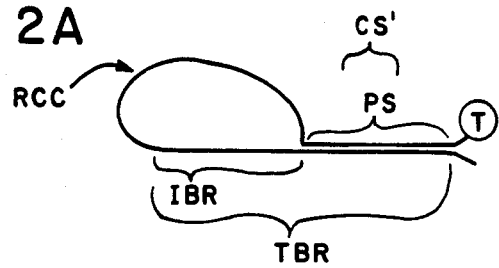

The present invention will first be discussed in terms of the displacement geometry of U.S. Ser. No. 607,885, involving a probe polynucleotide having a target binding region and a labeled polynucleotide bound thereto. The following terms are used herein in their ordinary meanings, as amplified in the previously-listed patent applications.

Polynucleotide or Polynucleotide Strand
Complementary (or Purine/Pyrimidine) Base Pairing
Hybridization
Probe Pdlynucleotide or Probe
Labeled Polynucleotide or Signal Strand
Reagent Complex
Nucleic Acid Construct or Covalent Displacement Complex (see U.S. Ser. No. 729,504)

In some cases (see FIGS. 2A-2D hereof and FIG. 1F of U.S. Ser. No. 729,504), it is convenient to consider a covalent displacement complex containing a single polynucleotide chain folded onto itself as two polynucleotide segments: the labeled polynucleotide segment including the pairing segment PS and tag T, and the probe polynucleotide including target binding region TBR. If a hairpin (HP) is present, it is convenient to consider the hairpin the divider between the labeled polynucleotide and the probe polynucleotide segments.

Sizes, types and geometries of probe polynucleotide (DNA or RNA), target binding region, labeled polynucleotide (DNA or RNA or DNA/RNA), and tags can be as set forth in any of the above-listed applications. Regions of perfect homology may be replaced by segment with limited numbers of mismatches as described in such applications. Target nucleotide sequences which can be analyzed, as in those applications, include viral or bacterial nucleic acid sequences, DNA or RNA sequences of plants, animals (including humans) or microorganisms (including plasmids) and rRNA (and other non-protein coding sequences). The invention may be used for either detecting and determining the concentration of an infectious agent or for distinguishing the strain, regulatory state or other state (including drug resistances) of an organism or vector.

This invention is an improved method for carrying out strand displacement assays including the assays of U.S. Ser. No. 607,885 of Diamond, et al. Capturing refers to hybridization of the displaced labeled polynucleotide to a second (or "capture") polynucleotide which is at least partially complementary to the labeled polynucleotide, in a region of the labeled polynucleotide substantially or completely within the segment (pairing segment PS) that had been bound to the target binding region TBR in the reagent complex. Thus segment PS (including that portion, CS' in the Figures, of PS to which the capture polynucleotide can specifically bind) is available for hybridization to CP only when PS has been displaced from TBR.

The capture polynucleotide also should have some property, or should be modified in some way, so as to make this capture polynucleotide separable from intact labeled displacement complexes (called reagent complexes in US. Ser. No. 607,885) as well as from other sources of background such as detached tags. Such modifications include attachment of the second polynucleotide to a solid support, such as bead, a filter, or a membrane, and attachment of affinity reagents such as biotin to the capture polynucleotide. Alternatively, the capture polynucleotide can be significantly larger than the unreacted displacement complex to allow a size separation after hybridization.

This invention is applicable both to displacement assays carried out on a solid support and to displacement assays carried out solely in solution. For solid support assays, capturing serves to reduce background signal in the assay which may result from the detachment of unreacted displacement complexes from the support due to breakage of the polynucleotide, failure of the attachment reaction, degradation of the solid support or other sources of non-specifically detached label. A second benefit is that the captured labeled polynucleotide can be removed from the displacement reaction and transferred to a position or condition which is more advantageous for readout. For solution assays, capturing provides a method for separating displaced labeled polynucleotides from unreacted displacement complexes. Captured labeled polynucleotide from solution assays can also be transferred to a position or conditions which are more advantageous for readout. Solution displacement reactions have the potential advantage of better hybridization kinetics than reactions on solid supports, and allow the use of polymers such as PEG (see U.S. Ser. No. 684,308 of Williams, et al.) to enhance these reaction rates. The combination of solid support displacement reactions with the use of capture polynucleotide has the advantage of potentially higher signal to noise ratios, due to two separation steps, and may be simpler to use.

The use of a capture strand bearing an affinity reagent such as biotin permits both the initial displacement reaction and the capturing reaction to be carried out in solution. Separation of the displaced probe is achieved by trapping captured labeled polynucleotides on an aviin support (such term being meant to also include immobilized streptavidin or antibiotin antibody). An additional advantage is that the displacement reaction can be carried out using an easily prepared complex (described in U.S. Ser. No. 729,504 of Fritsch and Collins, filed May 2, 1985) which contains the labeled polynucleotide and the target polynucleotide in a single polynucleotide strand. This "covalent displacement complex" simply unfolds after hybridization and strand displacement by the analyte, making the complement of the capturing polynucleotide (CS' in FIG. 2B hereof) single stranded and available for hybridization. Only covalent complexes which have hybridized to analyte should be captured.

The capture polynucleotide can be added after the displacement reaction has been completed, or can be present during the displacement reaction. In general, the concentration of capture polynucleotide will be greater than the concentration of target nucleotide sequence in the sample (i.e., the analyte), and can be greater or smaller than the concentration of reagent complexes. Since the analyte and capture polynucleotide will be homologous (in a complementary sense) over at least a portion of each sequence, analyte can first hybridize to the capture polynucleotide (see FIG. 2C hereof). Since the target nucleotide sequence is still available for hybridization to the target binding region of the displacement complex, this capture polynucleotide-analyte hybrid (the "first intermediate complex") can now hybridize to the labeled displacement complex. This second intermediate complex may be stable in this configuration, or may resolve by strand exchange and be recaptured. In either event, the displacement complex will only be captured when it has hybridized to analyte. If, however, second intermediate complexes are assayed as positive, some of the characteristics of a sandwich assay are imparted; and, therefore, some sample polynucleotides may be considered analyte which have regions complementary to different portions of the target binding region spaced too far apart to cause displacement with high efficiency or which are incapable of complete displacement for a variety of reasons.

The capturing reaction is compatible with many readouts including enzymes, poly A tails (see U.S. Ser. Nos. 729,502 and 729,503 of Vary, et al), fluorescent beads and enzyme substrates. In addition, capturing can occur in a defined space on a surface when the capture polynucleotide is already attached to a solid support. When a biotinylated (or other immobilizable) capture strand is used, labeled polynucleotides can be trapped at a particular position on a surface coated with avidin. An avidin coated "dipstick" could be used to trap captured labeled polynucleotides. Alternatively, avidin could be attached to surfaces to allow trapping in a predefined position for automated signal readout.

In a solution system, the capture strand provides the only means for separation (or the primary means if other steps are included), and must bind to displaced labeled polynucleotides with high selectivity (not binding to undisplaced reagent complexes). If the capture strand is immobilized or immobilizable onto a support, then the nonspecific binding of intact or broken reagent complexes to the support must be rare. The fraction of nondisplaced reagent complexes adhering to the support, either through nonspecific capturing or nonspecific binding to the support that would be permissable in the reaction is a function of both the initial number of reagent complexes and the number of analyte molecules to be detected. The relationship between these parameters is shown below:

| # Complexes | # Analyte | % Nonspecific | Signal | Noise |
|---|---|---|---|---|
| $10^8$ | $10^6$ | 1% | $10^6$ | $10^6$ |
| $10^8$ | $10^6$ | 0.1% | $10^6$ | $10^5$ |
| $10^8$ | $10^6$ | 0.01% | $10^6$ | $10^4$ |
| $10^{10}$ | $10^6$ | 0.01% | $10^6$ | $10^6$ |
| $10^8$ | $10^5$ | 0.01% | $10^5$ | $10^4$ |

As shown, in a reaction with $10^8$ reagent complexes, $10^6$ analyte molecules can only be detected with a (signal & background)/background ratio of at least 2/1 if background nonspecific binding is less than 1%. As the fraction of nonspecifically bound complexes decreases, the signal to noise ratio increases, with a resulting increase in assay sensitivity.

In many cases, it is expected that capture alone can provide adequate specificity to a solution displacement assay. However, in some cases, capturing can be combined with both probe immobilization and/or release of capture tag from a support (see below).

The present invention is further described herein in relation to the Figures. A discussion of the preferred features of the capture strand in the present invention follows the description of the Figures.

FIG. 1A shows two reagent complexes on a support, having probes $P_1$ and $P_2$. Each probe has an identical target binding region TBR. A labeled polynucleotide or signal strand ($L_1$ and $L_2$, respectively) is bound to a portion of each TBR with the portion of the labeled polynucleotide $L_1$ so-bound designated PS for pairing segment, and the portion of TBR not bound to PS designated IBR for initial binding region.

In FIG. 1B, a sample strand G containing the target nucleotide sequence TNS (homologous in a complementary sense to TBR) has bound to the initial binding region IBR of probe $P_1$. The reagent complex including probe $P_2$ is unchanged (intact). At this point, the top reagent complex is subject to strand migration and ultimately displacement of segment PS from TBR, as discussed in U.S Ser. No. 607,885. The result, shown on the left of FIG. 1C, is that G is bound to $P_1$, via TNS and TBR and that $L_1$ is displaced into solution. Thus far, the assay of several earlier applications has been described. It should be appreciated, however, that intact reagent complexes (such as that containing $P_2$ in FIG. 1C) will normally be present at a 100-fold, 1000-fold or greater excess relative to displaced labeled polynucleotides ($L_1$ in FIG. 1C). If any such intact reagent complex separates from the support at the point of attachment, or if separation occurs at any point along the strand to the left of TBR, or if the tag T detaches from $L_2$, then detectable tag other than the displaced labeled polynucleotide $L_1$ will be in solution.

On the right of FIG. 1C, a portion CS' of the pairing segment PS of the labeled polynucleotide is shown. A capture polynucleotide CP (or capture strand) is shown in immobilized form, with a capture segment CS which is complementary to segment CS' of labeled polynucleotide $L_1$. After the displaced labeled polynucleotide $L_1$ is in solution, it can hybridize to CP via CS'/CS, forming the captured structure shown in FIG. 1D.

Comparing the intact reagent complex at the bottom left of FIG. 1C with the capture structure shown in FIG. 1D, it can be seen that most forms of background signal which may be non-specifically released into solution will not specifically bind to CP. If $P_2$ either detaches from its support or breaks near its left end, then the hybrid released into solution does have a segment homologous to CS' of labeled polynucleotide $L_1$ within labeled polynucleotide $L_2$, but such segment is in the middle of a double-stranded segment and is thus not available for hybridization to segment CS. If the tag T breaks off, then it has no polynucleotide sequence specific for the capture strand CS. The only form of non-specific signal likely to bind to capture polynucleotide CP with high efficiency is any intact or nearly intact labeled polynucleotide $L_2$ which melts from probe $P_2$. The gel electrophoresis results of the earlier patent applications show that this is not a likely source of significant background. Of course, one should still seek to avoid such melting and also avoid the presence of labeled polynucleotides which never bound to probes (e.g., those adsorbed non-specifically to the support).

FIG. 2A illustrates a reagent complex construct RCC made by the techniques of U.S. Ser. No. 729,504 having a target binding region TBR near one end and a pairing segment PS near the other end, with a tag T on the end near the pairing segment PS. The pairing segment PS is hybridized to the end-most portion of TBR, leaving the interior portion IBR of TBR single-stranded. No hairpin structure separating TBR from PS is shown in FIG. 2A (but it may be present).

Figure 2B:
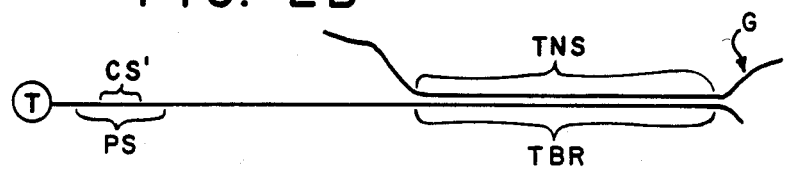

In FIG. 2B, a sample polynucleotide G having a target nucleotide sequence TNS has bound to IBR (IBR is shown in FIG. 2A) and displaced segment PS from TBR, forming a complete TNS/TBR double-stranded segment. The pairing segment PS, adjacent to the tag T, is now in single-stranded form. An interior (intermediate) portion of the pairing segment PS is designated CS'.

Figure 2C:
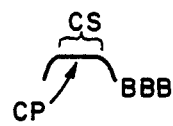

In FIG. 2C a capture polynucleotide CP is shown with a capture segment CS complementary to portion CS' of pairing segment PS. The capture polynucleotide CP also has a series of attached biotin moieties (shown as B's). Biotin may be attached enzymatically, chemically, or photochemically.

Figure 2D:
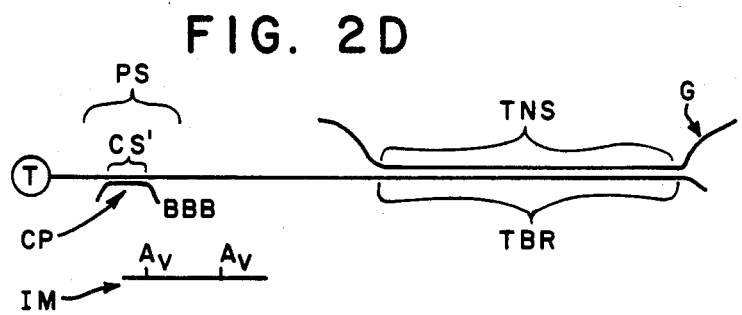

In FIG. 2D, the hybrid between the opened reagent complex of FIG. 2B and the capture polynucleotide CP of FIG. 2C is shown. The pendant biotins can now bind to immobilized avidin (shown as Av on support IM). Comparing FIG. 2A to FIG. 2D, it is seen that segment CS' is unavailable in the intact reagent complex construct RCC for hybridization to capture polynucleotide CP. Accordingly, capture polynucleotide CP can efficiently separate reagent complex constructs which have been hybridized to sample polynucleotides G having TNS from those reagent complexes which have not been contacted by target nucleotide sequence TNS.

Once the capture polynucleotide CP has bound to the support IM via biotin/avidin, the solid phase can be separated from the liquid phase. Tag T attached to the solid phase can now be determined. Alternatively, the tag T may be specifically released into a fresh solution phase in a variety of ways: (1) displacement with dissolved biotin (see Examples 11-14), (2) melting the double-stranded segment CS/CS' (if it is sufficiently short), (3) displacement with either (a) a strand complementary to more of PS than is CS' or (b) a strand complementary to more of CP than is CS or (4) specific chemical cleavage of the link between tag T and segment PS. Modes of release are preferred which do not operate on reagent complexes non-specifically bound to support phase IM; thus, in many cases, displacement modes (1) and (3) are preferred.

The scheme shown in FIGS. 2A-2D is available whether the capture polynucleotide CP was present during hybridization of G to IBR or not. Nevertheless, it is not the only mechanism available, especially when RCC, CP and sample are all admixed together. It should be apparent from FIGS. 2A, 2B and 2C that the target nucleotide sequence TNS can, and usually does, contain a segment identical to segment CS' and thus complementary to segment CS, or functionally identical in ability to form a stable hybrid with segment CS under the conditions employed. Thus, especially where capture polynucleotide CP is provided in excess relative to reagent complex construct RCC (each is generally in excess relative to TNS), the capture polynucleotide CP may bind to part of TNS, forming a first intermediate structure shown in FIG. 2E. Most of TNS remains single-stranded in this structure, including a portion (designated IBR') of TNS which is complementary to IBR of TBR.

Figure 2E:
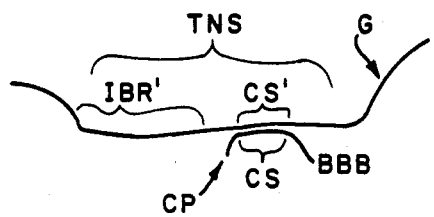

The first intermediate, shown in FIG. 2E, may still bind to the reagent complex construct RCC shown in FIG. 2A, with IBR' binding to IBR, forming a second intermediate structure. Strand migration at this point will normally lead to formation of a completely double-stranded TNS/TBR segment. Thus, the structure of FIG. 2B should form, with both PS displaced from TBR and CS displaced from the CS' portion of TNS. The same capture polynucleotide CP, or a different such molecule, may now bind to portion CS' of pairing segment PS. If, however, the CP/TNS/RCC second intermediate formed when IBR' binds to IBR is stable (strand migration does not displace CP and PS), then such second intermediate may be a second source of signal specifically bound to support IM. It may, however, be desirable to avoid the formation of first and second intermediates or to allow such second intermediates ample time to resolve by branch migration before the original reaction mixture (liquid phase) is removed from support IM. Any such intermediates present at the time when original reaction mixture is removed from support IM may subsequently complete strand migration and thus detach the signal, unless the particular displaced CP molecule (or and adjacent one on the solid phase also bound to avidin) can find the simultaneously displaced PS segment.

One experiment (see Example 8) with a reagent complex having distinct probe and labeled polynucleotide strands suggests that such second intermediate may resolve in such fashion to a major extent under certain conditions.

FIG. 3A illustrates an inverse reagent complex construct IRCC an embodiment of the invention of Collins et al, U.S. Ser. No. 809,992, filed herewith. It is constructed like the reagent complex construct RCC of FIG. 2A except that the detectable tag T is now on the end adjacent to the target binding region TBR. Region TBR plus such end and tag are considered the labeled probe polynucleotide. The pairing segment PS (bearing no tag) near the opposite end of the strand is bound by complementary base pairing to the portion of TBR nearest to tag T. A sample polynucleotide G containing the target nucleotide sequence can now bind to the single-stranded portion of TBR and then displace PS from TBR by strand migration as discussed above. The resultant hybrid is shown in FIG. 3B, with the single-stranded pairing segment PS containing a portion CS'.

FIG. 3C illustrates the hybrid of FIG. 3C subsequently bound by an immobilized capture polynucleotide CP to its solid phase. The capture polynucleotide CP contains a portion CS complementary to CS', and thus will capture the hybrid shown in FIG. 3B, but not the intact inverse reagent complex IRCC shown in FIG. 3A. Intermediate structures similar to those shown in FIG. 2E (and discussed in connection therewith) are also possible in many cases. As with the embodiments discussed there, it may be desirable in using the inverse reagent complexes IRCC shown in FIG. 3A, to employ proportions, orders of addition or other parameters to either avoid or fully resolve any such second intermediate structures (CP/TNS/IRCC) as may form.

The lengths of target binding region TBR, initial binding region IBR, segment PS, initial binding region IBR and heterologous portions of the probe polynucleotide and of the labeled polynucleotide can, in general, be any of the suitable or preferred lengths indicated in U.S. Ser. No. 607,885 and the above-listed subsequent U.S. pat applications. Thus, for example, preferred ranges include about 50-1000, nucleotides for IBR, 20-1000 nucleotides for PS (equal in size to LB in the Figures of U.S Ser. No. 607,885), 70-2000 nucleotides for TBR and 0-15 nucleotides of PS binding to the probe outside of TBR (to a region identified as RBR in FIG. 1G of U.S. Ser. No. 607,885).

The portion CS' of PS to which the capture polynucleotide can specifically bind once PS is displaced from TBR can be all of PS or most of PS or at one end of PS; it is preferred, however, that each end of CS' be located at least 25, and preferably at least 50 nucleotides from each end of PS (that is, be an intermediate segment of PS). Such an intermediate segment has reduced susceptibility to becoming momentarily single-stranded under circumstances (sometimes called "breathing") in which the PS/TBR duplex reversibly unwinds (only to subsequently rewind and thus not separate). Since such breathing is more likely to occur at an end, pairing segment (PS) which have CS' segments that include nucleotides at an end of PS may be captured by capture strand CP even without displacement by TNS having occurred. Such non-specific capture could result in non-specific signal detection unless the rewinding of TBR and PS was effective to displace such capture polynucleotides which had been non-specifically bound to PS.

The length of segment CS' within segment PS (and thus also the length CS within the capture polynucleotide CP) is preferably at least 25 nucleotides and more preferably 50-500 nucleotides. At the lower end of the more preferred range for CS' (50 nucleotides), it is preferred that PS be at least 100 nucleotide in length (to permit 25 nucleotides on each side of CS') and more preferred that PS be at least 150 nucleotides in length (to permit 50 nucleotides on each side of CS').

Random introduction of breaks ("nicks") into the normally intact labeled polynucleotide, either prior to or during the capture event, can be a source of non-specific signal. Such non-specific signal can also be reduced by the portion of the pairing segment complementary to the capture polynucleotide being internally located within the pairing segment. The prefered segment lengths and positions of the pairing segment and capture strand described above reduce or eliminate both non-specific capture due to breathing and non-specific signal detection due to such nicking.

While the above discussion is phrased in terms of one TBR and one PS segment, multiple PS segments binding to portions of the same TBR (as in FIG. 6 of U.S Ser. No. 607,885) are contemplated. Also contemplated are multiple TBR regions of the probe, with a labeled polynucleotide having a separate (and different) pairing segment PS bound to each. See U.S. Ser. No. 777,796 of Fritsch and Collins. In most cases, the capture polynucleotide need bind specifically only to the PS segment of a labeled polynucleotide which had been displaced by sample target nucleotide sequence when that displaced pairing segment has been separated from the immobilized or immobilizable probe.

Embodiments are also contemplated using multiple reagent complexes to simultaneously contact a sample to assay for multiple target nucleotide sequences. In such case, one or more capture polynucleotides can be used to separately isolate each group of displaced labeled polynucleotides for separate detection of tags, indicative of the presence and amount of each target nucleotide sequence. Such separate reagent complexes can be replaced by a probe having multiple labeled polynucleotides attached, each to a portion of a specific target binding region. Additionally, the several labeled polynucleotides can be captured simultaneously, but then released for detection sequentially.

As with the TBR/TNS binding and the PS/LBR binding described in the earlier applications, the CS/CS' binding described herein need not be perfect, but may include a limited number of mismatches (or deletions or other loop-forming sequences), so long as such mismatches are insufficient in number to prevent the desired specific binding or (considering the topology and size of PS and TBR) to inhibit the desired hybridization of CS to CS' or to cause non-specific melting of the CS/CS' duplex. One example where mismatches may be present is where the binding of TNS to TBR is perfect and the binding of CS to CS' (a portion of PS) is perfect, but the binding of PS to LBR or PS' (a portion of TBR) contains mismatches. Such example may prevent rehybridization of CS' to TBR leading to reversal of displacement and loss of signal. This approach may be especially useful for covalent reagent complexes where following displacement the displaced pairing segment is held in close proximity to the TBR. Concerning PS/LBR pairing, no regions of the labeled polynucleotides should be in a single-stranded form, (e.g., in loops) that can hybridize to capture polynucleotide without displacement.

It is also desirable to avoid complementarity of significant size (in general, greater than 10-25 nucleotides depending on sequence, melting temperatures and reaction conditions) between the capture polynucleotide (either region CS or heterologous regions outside of CS) and regions of the labeled polynucleotide outside of PS or between the capture polynucleotide and the probe polynucleotide (either within TBR and especially IBR, or outside of TBR). Such complementarity can result in hybridization of labeled reagent complex to the capture polynucleotide in the absence displacement, resulting in increased background.

Of the various permutations of reagent complex topology and capture polynucleotide, it should be appreciated that either immobilized or immobilizable capture polynucleotides may be used for either solution or solid phase displacement assays employing either: (1) covalent reagent complexes, (2) reagent complexes with distinct labeled polynucleotides and probe polynucleotides or (3) covalent inverse reagent complexes. While covalent attachment has been used herein as an exemplary means for attaching probes or capture polynucleotides to solid support or to attach pairing segments to target binding regions, other form of attachment such as stable hydrogen bonding (e.g., complementary base pairing) can be employed. Such other forms of attachment, and especially complementary base pairing, can also be employed for post-capture immobilization of an immobilizable capture polynucleotide (e.g., poly-dC on CP immobilized by oligo-dG-cellulose, or similar immobilization by sequences of CP outside of segment CS binding to complementary sequences on a strand immobilized to a solid support or otherwise separable, e.g., by virtue of size).

While the tag has been illustrated in the FIGS. as on an end of a nucleic acid strand, other forms of single or multiple tags incorporated in or on the appropriate polynucleotide segment or strand can be used. The important features of the tag are that it be directly or indirectly detectable and that it be positioned or attached to remain after displacement and capture with the appropriate strand or segment (PS in most cases).

The various reaction conditions (e.g., temperature, salt concentration, presence of agents such as recA protein and cofactor or polymers such as poly(ethylene glycol)) can be as in the earlier applications, with the additional proviso of not destabalizing the CS/CS' pairing, once formed.

In general, the number of capture polynucleotides should exceed the number of expected displaced pairing segments PS. Accordingly, in the usual case where the number of reagent complexes exceeds the anticipated level of target nucleotide sequences TNS, the number of capture polynucleotide sequences should also exceed anticipated levels of TNS, preferably by a factor of at least 10, more preferably by a factor of at least 100. Thus with $10^6$ expected analyte strands having TNS, whether there are $10^7$, $10^8$, $10^9$ or $10^{10}$ reagent complexes employed, there should be at least $10^6$, preferably at least $10^7$, more preferably at $10^8$ and commonly $10^9$–$10^{10}$ molecules of capture polynucleotide employed. In such cases, the molar ratio between reagent complexes and capture polynucleotides used in the same assay method (or present in the same kit) can be seen not to have independent significance, but rather to vary within the range $10^4$:1 to 1:$10^4$ reagent complexes to capture polynucleotides, or even outside of such broad range. However, the minimum number of capture strands that may be present is determined by the minimum number required to hybridize a sufficient fraction of displaced labeled strands in order to result in a signal of the desired intensity within the desired period of time.

EXAMPLES

Example 1—Displacement of labeled oligonucleotide followed by capturing DNA immobilized on latex beads Four DNA preparations containing human albumin cDNA sequences were used. Alb2A and Alb4A were constructed by digesting an Alkaline Phosphatase-Albumin clone with Xbal and Pstl. The (aproximately) 1.1 kb fragment was cloned into Xbal-Pstl cut M13mp10 (Alb2A) or M13mpll (Alb4A). The albumin clone B6 was digested with Pstl and the (approximately) 1.1 kb fragment (extending from the 19th nucleotide of the mature coding sequence to the Pst I site in the albumin gene (see Lawn, et al.) NAR, vol. 9, pp. 6103–6114 (1981) was cloned in to the Pstl site of M13 mp7 (mp7AlbPst). DNA was excised from the M13 phage of mp7AlbPst and covalently attached to 1 micron latex beads (Preparation #375-59-11) (see application U.S. Ser. No. 729,900, of Brown, et al for attachment chemistry). The fourth DNA was a synthetic 32 base oligonucleotide having the sequence 5'TCCTTTGCCTCAG-CATAGTTTTTGCAAACATG3'complementary to Alb4A and ... mp7AlbPst and having the same sense as Alb2A.

A displacement complex was prepared by incubating 0.44 pm of single stranded HaeIII cut Alb4A with 0.1 pm of a 32P-kinased 32 base complementary oligonucleotide in a total of 100 μl of 0.5M NaCl, 10mM EDTA, 0.1M sodium phosphate buffer, pH 6.8, and 0.1% SDS for 2 hours at 45° C. After incubation, a 5 μl aliquot (Al) was removed for gel analysis. Two displacement reactions were set up by incubating 45 μl of the above displacement complex either alone (reaction B) or with 0.2 pm of single stranded HaeIII cut Alb2A (reaction C) at 45° C. for 60 minutes in a total volume of 100 μl in the hybridization buffer described above. After the displacement reaction, two capturing reactions were set up by adding to each displacement reaction 8 μl of latex beads which had a total of 0.32 pmol of DNA covalently attached to them. A 10 μl aliquot (BO-10; CO-10) and a 25 μl aliquot (BO-25; CO-25) were removed from each reaction immediately after addition of the beads. The rest of the reaction was incubated for 50 minutes at 45° C. and 10 μl aliquots (B50-10; C50-10) and 25 μl aliquots (B50-25; C50-25) removed at the termination of the incubation. Aliquots A1, BO-10, CO-10, B50-10 and C50-10 were all analyzed directly by electrophoresis on a 1.6% agarose gel and autoradiography. DNA hybridized to beads remains at the top of the gel, while displacement complex and free 32 mer enter the gel and separate.

In the absence of analyte, no displacement of 32 mer was observed, and in the presence of analyte, approximately 95% displacement was observed. Some displacement occurred during the displacement reaction and some during the capturing reaction. Capturing with DNA beads in the presence of analyte resulted in approximately 10 fold more signal being associated with the beads than in the absence of analyte. "Capturing" in the absence of analyte derives from 32 mer which did not hybridize to Alb4A in reaction A. This experiment demonstrates that latex beads with DNA attached which is complementary to the signal strand of a displacement complex can effectively be used to capture displaced signal strands. The 25 μl aliquots were twice diluted 20–32 fold into hybridization buffer and pelleted by centrifugation. The second pellet was resuspended and analyzed by electrophoresis as above. Some of sample C50-25 was lost, resulting in a reduced signal. However, the washing effectively separated displacement complex and free 32 mer from the captured 32 mer demonstrating a method of reducing background and capturing a displaced polynucleotide.

EXAMPLES 2–10

Construction of a Series of Model Polynucleotide Analytes, Displacement Complexes, and Captures The following experiments described in this application use a series of model polynucleotides to demonstrate the capturing concept. See FIG. 4 for a diagram of nucleic acids described below.

I. Displacement complexes: Displacement complexes were prepared from a nucleic acid construct made by the methods described in U.S. Ser. No. 729,504 (Fritsch and Collins). The pMLC12/13deltaM7IVRTL construct, described and illustrated in FIG. 4D of that application, contains fragments from the human albumin gene cloned as inverted repeats in an M13 origin plasmid. These fragments were cloned into the center of a small inverted repeat derived from the M13mp7 polylinker. Single stranded forms of this construct fold up into a stem loop structure. Cleavage of the mp7 polylinker with a restriction enzyme releases the stem loop structure from the single stranded vector backbone. This insert can be used directly as a (1.6 kb nucleotide) covalent displacement complex with a 0.5 kb Bgl II-Hinc II albumin fragment as the signal strand, and a 1 kb Bgl II-Pvu II albumin fragment nucleotide target binding region (such nucleotide numbers are approximate). In single stranded complexes the target binding region is located 22 nucleotides from the 5' end and the signal strand 41 nucleotide from the 3' end.

pMLC12/13deltaM7IVRTL contains an additional inverted repeat (IVRTL) located at the inside edge of the signal strand, which forms a 52 nucleotide (26 base pair, see FIG. ID of U.S Ser. No. 729,504) hairpin containing a double-strande E RI cleavage site in single stranded forms of this construct. Cleavage at both the Bam HI site in the mp7 polylinker and at the IVRTL Eco RI site results in the formation of a displacement complex in which the signal strand and target strand are held together only by base pairing. We will distinguish between these two forms of the construct in which the IVRTL hairpin is or is not cleaved by Eco RI by referring to them as the covalent complex and the non-covalent complex, respectively.

p66b was constructed by gel-isolating the double-stranded PvuII fragment containing the sequence for the entire displacement complex from pMLC12/13deltaM7IVRTL and ligating it to the gel-isolated Pvu II backbone of the M13 origin plasmid pUC119. Single stranded forms of this construct were produced as previously described for pMLC12/13deltaM7IVRTL, except that the DNA was transformed into the E. coli host strain MV1193 obtained from Dr. Michael Volkent/ (JM 101 del(srIR-recA) 306:Tr10), and superinfections are routinely done with bacteriophage M13K07. The resulting displacement complexes are identical to those produced by pMLC12/13deltaM7IVRTL; this method is preferred only due to higher yields of the displacement complex. Inverse reagent complexes used in Examples 9 and 10 result from labelling of the 5' end of p66b.

p66d was constructed as described for p66b, except that the PvuII fragment was inserted into the pUC119 vector in the opposite orientation. The single stranded form of p66d produced after superinfection contains a displacement complex which is the complement of the p66b strand. Thus, before cleavage in the IVRTL hairpin, displacement complexs made from p66b contain the signal strand at the 5' end and the target binding region at the 3' end.

II. Model Analytes: Model analytes were constructed by gel purifying a 2 kb Hind III-Eco RI fragment from a plasmid, pAllAlb, which contains the entire cDNA sequence of human albumin. The HindIII site is the HindIII site in the 3' end of the albumin cDNA. The EcoRI site is present in adjacent vector sequences. The vector sequences present on the HindIII EcoRI fragment have no bearing on the following examples. The HindIII - EcoRI fragment was ligated into Hind III-EcoRI digested M13mp8 and M13mp11 to give mp8Al-lAlb and mpll.AllAlb, respectively. Single stranded DNA was purified from phage containing these constructs, and was partially digested with Hae III to linearize these model analytes. There are no HaeIII sites within the albumin cDNA sequence. mp8.AllAlb complementary to the target binding region of p66b displacement complexes, and mp11.AllAlb template DNA is complementary to the TBR of p66d displacement complexes.

III. Model Capturers: Several different model capturers were constructed to help define the best geometry for capturing nucleic acid constructs.

c1. mp18.AlbTaqPst (C1A) and mp19.AlbTaqPst (C1B) were constructed by gel purifying a 350 base pair Bgl II-Pst I fragment from a human albumin cDNA clone, digesting it with Taq I, and ligating the resulting 280 base pair fragment into Acc I-Pst I mp18 and mp19 vectors. mp19.AlbTaqPst is complementary to the pairing segment (PS') of the labeled strand of p66b. mp18.AlbTaqPst is complementary to the pairing segment in p66d.

c2. mp8.AlbBH was made by ligating the 500 base pair Bgl II-Hinc II fragment from albumin cDNA into the Sma I site of mp8. The insert in mp8.AlbBH is coextensive with and complementary to the pairing segment in the p66b displacement complex described above.

c3. mp7delta.AlbXba constructs 1+, 2+, 3−, and 4− were made by digesting mp19.AlbTaqPst Rf DNA with Xba I and end filling, gel purifying the resulting 300 base pair fragment, and ligating it to the 6800 base pair gel purified Pvu II vector backbone fragment of mp7. Two resulting phage isolates containing single stranded albumin DNA complementary to the labeled polynucleotides of p66b displacement complexes are labeled 1+ and 2+, while two phage isolates containing the albumin strand complementary to probe polynucleotide strands of p66b are labeled 3− and 4−. Constructs 1+ and 2+ differ from mp19.AlbTaqPst in that a portion of the lac gene and all polylinker cloning sequences are deleted from the mp7delta backbone, and in that the albumin insert is complementary to a more interior portion of the signal strand (see FIG. 4).

c4. Biotinylation of mp7deltaAlbXbal+ and mp7deltaAlbXba3− DNA using Vector Laboratories Photoprobe ™ Biotin.

The capturing strands mp7deltaALbXbal+ or mp7deltaAlbXba3− were biotinylated using the commercially obtained Photoprobe Biotin (Vector Laboratories) essentially as described by the manufacturer and repeated below.

Photoprobe ™ biotin (500 μg) was resuspended in 500 microliter water as recommended by the manufacturer and stored in the dark at −20° C. 10 micrograms of template DNA from the clone mp7 deltaAlbTaqXbal+ or mp7deltaAlbXba3− was ethanol precipitated and resuspended in 10 microliter H$_2$O. The DNA was mixed with 10 microliter Photoprobe biotin solution under a safelight, sealed in a glass microcapillary pipette and irradiated by a sunlamp (GE infrared lamp 2JOR40/1) for 20 or 30 minutes in separate reactions. The sample was kept in an ice-H$_2$O bath during the entire irradiation procedure. After irradiation, the sample was removed from the capillary, diluted with 100 microliters of 0.1 M Tris-HCl, pH 8.0, extracted twice with 2-butanol and precipatated following addition of 1/10 volume 3M Na Acetate and 2 volumes of ethanol. The precipatated sample was resuspended in 10 microliters 0.1 mM EDTA, pH 8.0.

Successful reaction was monitored by taking an aliquot of the biotinylated DNA and hybridizing a 32-P labeled oligonucleotide (cALB 32-mer, the complement of the 32 mer described in Example 1) complementary to a 32 base segment of the capture strand. One-half of the sample (control) was then electrophoresed directly on an agarose gel. The other half was mixed with 10 microliter of streptavidin latex beads supplied from Pandex Laboratories in 0.2M NaCl, 20 mM Tris-HCl, pH 8.0, 0.1% NP-40 for 10–20 minutes at room temperature. After the binding step, the beads were removed from the solution by centrifugation (2 minutes, Eppendorf centrifuge) washed once and the combined solution phases were electrophoresed in a parallel lane to the control sample. Following electrophoresis and autoradiography, the results indicated that nearly all the 32-P labeled oligonucleotide sample that was hybridized to the mp7deltaAlbXbal+ DNA was removed from the sample that was exposed to the streptavidin agarose, indicating that the majority of template DNAs (capture strands) had at least one biotin group attached.

Example 2—Displacement and Capture using Bam HI cut p66b covalent complex and mp19albTaqPst capturer Single stranded p66b DNA was isolated, digested with Bam HI, and 3' end labeled by incorporation of 32PdATP with the klenow fragment of DNA Pol I (the other nucleoside triphosphates being present in unlabeled form). This treatment inserts an adenine nucleotide opposite the underlined thymidine in the following terminal portion of the displacement complex:

```
5'-GATCCGTCCGTCGACC...
3'-    GCAGGCAGCTGG...
```

The labeled covalent complex was then gel purified away from other labeled material, including the vector. The gel purified, 3' end-labeled covalent complex was diluted to 0.005 pm/μl in TE, as estimated by comparision to DNA standards on an ethidium stained gel.

Displacement and capturing were performed simultaneously by incubating 0.01 pm of complex with varying amounts of Hae III digested mp8.AllAlb template DNA (analyte), and 0.1 pm of either mp7 template DNA (mock capture) or mp19.AlbTaqPst template DNA in a total of 20 μl of 0.3M NaCl and 0.1M Tris HCl, pH 8.0, for 60 minutes at 65° C. The reactions were then run on a 1% agarose gel to separate unreacted complexes from complexes that had hybridized to analyte, and from complexes that had hybridized to analyte and to capturer. The gel was then dried and autoradiographed overnight at −80° C. with a screen. Because a covalent displacement complex was used, hybridization of heterogenoeously sized analyte DNA resulted in the appearance of several higher MW bands on the gel. The addition of 0.001, 0.005, 0.01, or 0.05 pm of analyte DNA resulted in an increasing amount of displacement, with complete displacement observed with 0.01 or 0.05 pm of analyte. When 0.1 pm of mp19AlbTaqPst DNA were added to duplicate reactions, all of the analyte-displacement complex hybrids were captured, as indicated by the presence of new higher MW bands on the gel. This indicated that covalent complexes can be successfully displaced and captured, and that capturing is dependent upon displacement.

However, when 0.1 pm of mp19.AlbTaqPst DNA was added to the complex in the absence of analyte, a significant background level of capturing (about 20%) was observed A similar level of non-specific background capturing was seen in a reaction with 0.01 pm analyte and 0.1 pm mp7 DNA, suggesting that this background capturing results primarily from labeled fragments which are hybridizing to the M13 vector portion of the capturing strand. The experiments that follow demonstrate that this non-specific capturing results from labeling methods which may introduce nicks into DNA, incomplete purification, and small sequence homologies between the M13 vectors and the cloning sites used to construct p66b, and that non-specific capturing is not an inherent property of the capturing concept.

Example —Displacement and Capturing with an Xba I cut p66b cova complex and an improved labeling and purification protocol In this experiment, two changes were made to help minimize non-specific capturing observed in Example 2. Since the p66b complex is usually cut out by cleavage with Bam HI in the mp7 polylinker, this leaves small regions of M13 homology at the labeled (3') end of the molecule. A displacement complex was made which lacks this homology, by cleavage of p66b at the Xba I site within the signal strand-target strand hybrid. Then, in order to minimize the isolation of contaminating labeled single stranded fragments which might cross hybridize with the capturer, the complex was first gel purified and then end labeled with Klenow as described above.

Reactions were carried out by incubating 0.01 pm of p66b Xba covalent complex (about 4000 Cherenkov cpm) with either 0, 0.05 pm or 0.005 pm of Hae III cut mp8.AllAlb analyte, and with either 0, 0.01 pm, 0.05 pm, or 0.25 pm of capturers mp19.AlbTaqPst, mp8.AlbBH, or mp7 as described above. The results were analyzed by autoradiography of a 1% agarose gel used to separate the molecules.

In this experiment, nonspecific capturing of about 1% of the displacement complexes was observed in the absence of analyte with all three capturers, although 0.25 pm of mp8.AlbH gave a slightly higher background of about 3%. When 0.005 pm of analyte were added to reactions with 0.01 pm complex and either 0.05 pm mp19.AlbTaqPst or 0.05 pm mp8.AlbBH, approximately 50% of the complexes were displaced; all displaced complexes were captured. When a 5 fold excess of analyte was used (0.05 pm), 100% of the complexes showed displacement. The addition of 0.01 pm of either capturer resulted in capture of less than 50% of displaced complex; with 0.05 or 0.25 pm of mp19Alb-TaqPst or mp8AlbBH capturing was essentially complete. It should be appreciated that the excess analyte in these cases can bind to capture strands, necessitating higher levels of capture strand to achieve essentially complete capture efficiency.

Example 4—Labeling of p66b Xba I complex by ligation of a kinased oligonucleotide results in decreased non-specific capturing In this experiment, p66b Xba complex was labeled by ligating a kinased oligonucleotide to the 3' end of the molecule. 10 pm of a 15 base oligonucleotide with the sequence 5' CTAGAGGCCTCTGCA3' was labeled at the 5' end with 32P -gamma ATP and polynucleotide kinase (see Maniatis et al, Cloning Manual (Cold Spring Harbor Laboratory 1982)). The labeled oligonucleotide was purified away from unincorporated 32P -rATP by centrifuging the reaction twice at 6000 rpm for 30 minutes in a total volume of 500 μl of TE in a Centricon 10 filtration device from Amicon. The kinased oligonucleotide and 1 pm of Xba I cut p66b gel purified complex were precipitated together with ethanol, and resuspended in 14 μl of TE. 4 μl of 5X ligase buffer (Maniatis et al Manual) and 2 μl of DNA ligase were added and the reaction was incubated at 15° for 4 hours. The reaction was diluted to 50 μl with TE, heated to 42° C. for 10 minutes to melt any non-ligated oligonucleotides and electrop....horesed on a 1% agarose gel. Following electrophporesis, the gel was stained with ethidium bromide and viewed with a uv light box. Approximately 66% of the complexes ligated to each other, so that only 0.33 pm of complex were available for ligation to the kinased oligonucleotide. The kinased complex was purified and had an estimated specific activity of about $10^6$ cpm per pm.

Displacement and capturing reactions were carried out as described above (Example 3), except that reactions were incubated at 65° C. for only 45 minutes. Either 0.001 pm (1000 cpm) or 0.005 pm (5000 cpm) of displacement complex were used per reaction. In the absence of analyte, no non-specific capturing was observed in reactions with 0.001 pm of complex and 0.02 pm of either mp7, mp19, mp7deltaAlbXba3— or mp19.AlbTaqPst. The addition of 0.01 pm of analyte to these reactions resulted in 100% displacement, and in no detectable capturing in reactions with mp7, mp19, or mp7deltaAlbXba3—, and in greater than 90% captured complexes with mp19.AlbTaqPst. In reactions with 0.005 pm of complex, in the absence of analyte no detectable capturing was observed with mp7deltaAlbXba3—, less than about 0.5% non-specific capturing was observed with mp7, mp19 and mp19.AlbTaqPst. Slightly more background was observed with mp19.AlbTaqPst than with mp7 and mp19. In the presence of 0.01 pm of analyte, less than 1% capturing was observed with mp7, mp19, or mp7delta.AlbXba3—, while greater than 90% capturing was observed with mp19.AlbTaqPst.

These results indicate that lower background levels for non-specific capturing can be obtained using complexes which are labeled by ligation to a kinased oligonucleotide (or other techniques not causative of nicks). In addition, the absence of nonspecific capturing with mp7deltaAlbXba3— indicates that non-specific capturing at experimentally detectable levels is not an inherent property of the capturing concept.

Example 5—Comparison of mp7delta and mp19.AlbTaqPst capturers

In an attempt to decrease the amount of non-specific capturing observed in the absence of analyte, two modifications were made in the procedures of Example 4. 0.2 pm of the p66b Xba I complex labeled by oligonucleotide ligation described in Example 4 was prehybridized to 2 pm of mp19.AlbTaqPst DNA in a total of 50 μl of 0.3M NaCl and 0.1M Tris,pH8 for 60 minutes at 65° C. The complex was then gel purified away from this capturing template and any contaminating DNA fragments which hybridized to the capturing template. In addition, the mp7deltaAlbXba series of capturers were tested to determine if deletion of M13 related sequences would improve background capturing.

Either 0.001 pm (1000 cpm) or 0.005 pm(5000 cpm) of the pre-hybridized complex were incubated in the absence or presence of 0.01 pm Hae III cut mp8.AllAlb, and with either 0.02 pm of capturer (in 0.001 pm complex reactions) or 0.05 of capturer (in 0.005 pm complex reactions) using the same conditions described in Example 4.

In the presence of excess analyte, 100% of the displaced commmplexes were captured using either mp19.AlbTaqPst, mp7deltaAlbXbal+, or mp7deltaAlbXba2+, capturers with the proper orientation capture strand.

In the absence of analyte, no detectable background was observed with capturers mp7, mp19, or mp7deltaAlbXba3—. Both mp7 and mp19 are controls for nonspecific capturing due to cross hybridization to M13

DNA. mp7deltaAlbXba3- contains the complement of the capturing strand, and is a control for hybridization of the capturer to complexes by strand exchange and D-loop formation.

A small amount of background capturing (about 0.5%) was observed with capturers mp19.AlbTaqPst, mp7deltaAlbXba1+ and mp7deltaAlbXba2+. Approximately the same amount of capturing was observed with each. These capturers are complementary to the 3' end of (unlabeled end) the complex. Since appropriate controls eliminate the possibilities that background derives from M13 cross hybridization (mp7, mp19) or strand exchange between undisplaced reagent complexes and capture DNA (mp7deltaAlbXba3−), a likely explanation is that a small percent of the complexes are being nicked near enough to the 3' end to allow dissociation of the labeled fragment from the complex and rehybridization to the capturing strand. This suggests that background should be eliminated by using a complex and capturer combination such that the capturer can only hybridize to an internal portion of the displaced signal strand. Small nicked fragments would then not be captured. This idea is demonstrated in Example 6.

Example 6—Displacement and capturing with Bam HI p66b and mp7deltaAlbXba capturers Single stranded p66b DNA was digested to completion with Bam HI, and the covalent complex was isolated by gel purification. A 32P-kinased oligonucleotide with the sequence 5'GATCCGCGGCGGTAC3' was ligated to the 3' end of the complex as described in Example 4 except that 2.4 pm of the complex and 10 pm of the oligonucleotide were used in the ligation reaction. The specific activity of the resulting complex was estimated at $8 \times 10^4$ cpm/pm.

Reactions were done by incubating either 0.01 pm (1000 cpm) or 0.03 pm (3000 cpm) in the presence or absence of 0.01 pm Hae III cut mp8.AllAlb analyte, with 0.1 pm of capture DNA in a final volume of 20 µl of hybridization buffer (0.3M NaCl, 0.1M Tris HCl,pH8.0, and 10 mM EDTA) for 60 minutes at 65° C. Reactions were analyzed by gel electrophoresis and autoradiography as described in Example 3.

In the absence of analyte, no detectable background capturing was observed with any of the following capturers: mp7, mp19, mp7deltaAlbXba1+, mp7deltaAlbXba3− or mp7deltaAlbXba4−. The addition of 0.01 pm of analyte to reactions with 0.01 pm complex resulted in 100% displacement; no capturing was observed with the mp7deltaAlbXba4− capturer, and 100% capturing was observed with the mp7deltaAlbXba+ capturer. The addition of 0.01 pm of analyte to reactions with 0.03 pm complex resulted in approximately 50% displacement and no capturing with mp7deltaAlbXba4− and complete capturing of the displaced complexes with mp7deltaAlbXba1+.

Example 7—Capturing of displaced Bam p66b with biotinylated mp7deltaAlbXba1+ and trapping on streptavidin agarose p66b Bam complex was labeled at the 3' end by ligation of a 32P-labeled oligonucleotide and purified as described for Example 6. Biotinylated mp7deltaAlbXba1+ was used as the capturing strand. Four reactions were set up which included combinations of the complex, the capturer and the HaeIII cut mp8.AllAlb analyte as outlined in Table 1. All reactions were done in 50 µl of hybridization buffer, (see examples) and were incubated at 65° C. for 60 minutes.

TABLE 1

| REACTION | pm COMPLEX | pm ANALYTE | pm CAPTURER |
|---|---|---|---|
| 1 | 0.03 | 0.01 | 0.08 |
| 2 | 0.03 | 0 | 0.08 |
| 3 | 0.03 | 0.01 | 0 |
| 4 | 0.03 | 0 | 0 |

The reactions were then bound to about 100 µl packed volume streptavidin agarose (BRL) which had been washed twice in 500 µl of binding buffer (0.2M NaCl, 0.05M Tris HCl, pH8.0, 100 µg/ml sonicated salmon sperm DNA, 1 mM EDTA) and pelleted in an Eppendorf tube. Samples were diluted to 100 µl with binding buffer, transferred to the tube containing the streptavidin agarose pellet, mixed in an Eppendorf shaker for 1 minute and allowed to bind without shaking for an additional 2 minutes. The samples were then diluted to 500 µl with binding buffer, mixed for 2 minutes in the shaker, and centrifuged for 3 minutes to pellet the streptavidin agarose. The supernatents (Rinse 1) was removed and counted for radioactivity. The pellet was washed three more times with 500 µl binding buffer as for Rinse 1, and all supernatant (Rinses 2, 3, 4) and the pellet were counted. Rinse 1 was then rebound to a fresh 100 µl packed volume aliquot of streptavidin agarose (prewashed with binding buffer as before) in a 5 ml Sarstedt centrifuge tube which was rotated end over end for 15 minutes during binding. The agarose was pelleted by centrifugation, and the supernatant (Rinse 2B-1) saved and counted. The agarose was washed with 500 µl binding buffer for 15 minutes as above, followed by centrifugation and counting of the supernatant (R2B-2) and pellet (P2). The pellet was then reincubated with the R2B-1 supernatant for 45 minutes to determine if any additional binding would occur with a longer incubation. The agarose was then centrifuged, the pellet rewashed, and the pellet (P2') and two supernatants (R2'B-1 and R2'B-2) were counted. The results are shown in Table 2.

TABLE 2

| | COUNTS PER MINUTE | | | |
|---|---|---|---|---|
| REACTION: | 1 | 2 | 3 | 4 |
| pellet 1 | 478 | 13 | 36 | 25 |
| rinses 1-4 | 2554 | 2981 | 3303 | 3970 |
| % bound | 15.7 | 0.4 | 1.0 | 0.6 |
| pellet 2 | 581 | 40 | 80 | 50 |
| rinses (2B1-2) | 811 | 1982 | 2197 | 2117 |
| pellet 2' | 587 | 78 | 12 | 33 |
| rinses | 768 | 1957 | 1943 | 1969 |
| % bound (P1 + P2) | 35% | 3.0% | 1.4% | 1.5% |

This experiment demonstrates the use of a biotinylated capturer with a streptavidin agarose trap to collect the captured molecules. Only the reaction (Reaction 1) which includes all three components—the complex, the capturer, and the analyte—shows a significant amount (478+587 cpm; or 35% of total counts) of label bound to the support. In addition, this experiment illustrates that a 3 minute incubation of the reaction with the streptavidin agarose is insufficient to give complete trapping, substantially maximal trapping (581 cpm) occurred after 15 minutes of incubation, and a longer incubation did not result in any significant further trapping (587 versus 581 cpm).

Example 8—Comparision of displacement and capturing with covalent and non-covalent p66d complexes Covalent p66d displacement complexes were prepared and labeled at the 5' end by ligation of the kinased 16mer using the EF21splint as described in Example 9. The specific activity of the resulting complexes was about $1 \times 10^6$ cpm/pm.

Non-covalent p66d complexes were produced by complete digestion of approximately 50 μg of single stranded templated DNA with Bam HI and Eco RI. Complete digestion was ascertained by the appearance of equimolar amounts of three bands, corresponding to vector backbone, target strand, and signal strand, after electrophoresis of a small aliquot of the digest on an alkaline gel. Non-covalent p66d complexes were labeled at the 5' end of the signal strand as described for covalent complexes, by EF21 splint ligation of a kinased 16mer, with a resultant specific activity of $3 \times 10^6$ cpm/pm.

The four reactions outlined in Table 3 were set up in a total volume of 50 μl of hybridization buffer and incubated for 60 minutes at 65° C. using HaeIII digested mpll.AllAlb DNA as analyte and biotinylated mp7deltaAlbXba3—capturere. 10 μl of each reaction were analyzed by gel electrophoresis and autoradiography, and the remaining 40 μl by binding to steptavidin agarose. 200 μl packed volume streptavidin agarose was used per reaction. Binding and washing was as described in Example 10 (below), except that, after binding, the pellet was rinsed 3 times for 30 minutes at room temperature and once for 60 minutes at 65° C. The final pellet and all supernatants were counted. Data showing the cpm bound to agarose after each rinse are given in Table 3. These results show that displacement and capturing are approximately equally effective for covalent and non-covalent complexes.

Gel analysis of the same reactions, as well as two reactions in which only displacement complex and capturer were included, demonstrated that 100% of the complexes were displaced by analyte, and when capturer was included, 100% capturing occurred. In the absence of analyte, no capturing was observed. In addition, since complexes which have hybridized both to capturer and analyte (i.e., captured covalent complexes or the second intermediate) migrate differently from capturers which have hybridized only to signal strand displaced from noncovalent complexes, one can distinguish capturing intermediates ("second intermediates") which contain capturer hybridized to analyte which in turn is hybridized to the target binding region of the displacement complex, from those non-covalent complexes which have resolved to contain only capturer and displaced signal strand. In this experiment, approximately 90% of the captured signal is present in the resolved form, despite the fact that capture DNA was present in excess over analyte and complex, and would be likely to form the intermediate structure before displacement.

TABLE 3

| REACTION | pm COMPLEX | pm ANALYTE | pm CAPTURER |
|---|---|---|---|
| 1 | 0.2 covalent | 0.2 | 0.8 |
| 2 | 0.2 noncovalent | 0.2 | 0.8 |
| 3 | 0.2 covalent | 0.2 | 0 |
| 4 | 0.2 noncovalent | 0.2 | 0 |

| | CPM BOUND TO SUPPORT | | | |
|---|---|---|---|---|
| REACTION: | 1 | 2 | 3 | 4 |
| TOTAL: | 9821 | 26885 | 9318 | 30558 |
| RINSE 1: | 7932 | 24406 | 2403 | 5625 |
| RINSE 2: | 7383 | 22793 | 1267 | 1859 |
| RINSE 3: | 7055 | 20363 | 827 | 956 |
| RINSE 4: | 6186 | 19063 | 666 | 512 |
| FINAL | 5562 | 16718 | 304 | 299 |
| % Bound: | 55.6% | 62.1% | 1.7% | 1.0% |

Example 9 Large scale displacement and capture with trapping on streptavidin agarose.

The Bam p66b displacement complex was labeled to a specific activity of about $10^6$ cpm/pm by ligating a 32P-kinased oligonucleotide to the 5' end of the complex with the use of a 21 base splint (EF21). 10 pm of the kinased 16mer (indicated below by the asterisk), 10 pm of splint, and 1 pm of p66b Bam (underlined below) were incubated together at 22° C. for 15 minutes in 10 μl of 1X ligase buffer; 1 μl of ligase was added and the reaction incubated for an additional 30 minutes. The three molecules form the structure diagrammed below.

The four reactions outlined in Table 4 were set up in a total volume of 50 μl of hybridization buffer (see Example 6) and incubated for 30 minutes at 65° C. Hae III cut mpAllAlb and biotinylated mp7delta.AlbXba DNA were used as analyte and capturer, respectively. 25 μl of each reaction was then analyzed by gel electrophoresis and 25 μl by binding to streptavidin agarose as follows. 100 μl packed volume of streptavidin agarose was washed twice in 500 μl binding buffer in a 5 ml Sarstedt tube rotated end over end for 15 minutes, and pelleted by centrifugation. The 25 μl reaction aliquots were diluted to a total of 500 μl binding buffer, and incubated, rotating as above, for 15 minutes. The sample was transferred to an Eppendorf tube for centrifugation, the supernatant saved, and the pellet rewashed as above, once at room temperature for 15 minutes, then twice at 65° C. for 15 minutes, then for 60 minutes at room temperature and finally for 15 minutes at room temperature with TE. The final pellet and all supernatants were counted. Data showing the cpm bound to agarose after each rinse are given in Table 4. These results show that binding of complex to the support is dependent upon the presence of capturer and analyte, and on the amount of analyte present.

Gel analysis of the same reactions indicated that there is less than 0.05% non-specific capturing in these reactions. Specific capturing was more efficiently analyzed by gel separation, in that the presence of analyte resulted in capturing of approximately 80% and 20% of the complex in reactions 3 and 4, respectively.

It should be noted that this Example 9 and Example 10, below, provide labeling at the 5'-end, and thus adjacent to the target binding region rather than to the pairing segment. Such a geometry is described further in a copending application of Collins et al, Ser. No. 809,442, filed herewith.

TABLE 4

| REACTION | pm COMPLEX | pm ANALYTE | pm CAPTURER |
|---|---|---|---|
| 1 | 0.10 | 0 | 0 |
| 2 | 0.10 | 0 | 0.16 |
| 3 | 0.10 | 0.05 | 0.16 |
| 4 | 0.10 | 0.01 | 0.16 |

| | CPM BOUND TO SUPPORT | | | |
|---|---|---|---|---|
| Reaction: | 1 | 2 | 3 | 4 |
| TOTAL | 46435 | 42590 | 49423 | 41889 |
| RINSE 1: | 12915 | 10150 | 274308 | 15394 |
| RINSE 2: | 5254 | 3217 | 22982 | 10109 |
| RINSE 3: | 3911 | 2032 | 19978 | 7806 |
| RINSE 4: | 3500 | 1594 | 16261 | 6238 |
| RINSE 5: | 2203 | 1458 | 13780 | 5391 |
| RINSE 6: | 1482 | 1227 | 12351 | 4436 |
| FINAL: | 813 | 1044 | 10628 | 3658 |
| % BOUND: | 1.7 | 2.5 | 26.3 | 8.7 |

Example 10—Prehybridization of coplex and analyte, followed by capturing and trapping.

Two additional reactions were done using the Bam p66b complex described in Example 9. In these reactions, 0.1 pm complex alone (reaction 1) or 0.1 pm complex and 0.05 pm Hae III cut mp8AllAlb analyte (reaction 2) were incubated in 50 μl of hybridization buffer for 30 minutes at 65° C. 0.16 pm of biotinylated mp7deltaAlbXbal+ was then added to both reactions, which were then divided and treated as in Example 9, except that all rinses were at room temperature with binding buffer. By gel analysis, less than 0.05% non-specific capturing, and approximately 40% specific capturing was observed. The results of analysis on streptavidin agarose (Table 5) indicate that capturing and trapping occur with approximately equal efficiencies whether capture DNA is added after (as in this Example 10) or is present during (as in Example 9) the analyte-dependent displacement reaction.

TABLE 5

| | CPM BOUND TO SUPPORT | |
|---|---|---|
| REACTION | 1 | 2 |
| TOTAL: | 57860 | 55210 |
| RINSE 1: | 10364 | 18538 |
| RINSE 2: | 4360 | 14321 |
| RINSE 3: | 3046 | 11983 |
| RINSE 4: | 3035 | 9745 |
| RINSE 5: | 1781 | 8897 |
| FINAL: | 1124 | 7428 |
| % BOUND: | 1.9 | 13.5 |

EXAMPLES 11-14

Releasing Captured And Trapped Strands By Biotin Displacement

The following three Examples represent work by Edward Fritsch on the release by displacement with biotin nucleic acid strands that are immobilized by binding of biotins on the nucleic acid to avidin on the support. The displacement shown herein by dissolved biotin at moderate (22°-65° C.) temperatures represents an improvement and difference-in-kind compared to the near boiling (90° C.) treatment for 5 minutes of T. Kempe et al., *Nucleic Acids Research*, vol. 13, pp. 45-47 (1985) (see page 48), since at 90° C., melting of double-stranded DNA would occur. Examples 11 and 12 show the biotin-displacement of strands having both biotin and the label, evidencing that such can be conducted under conditions suitable for releasing the immobilized complexes of capture strand and labeled polynucleotide, or of capture strand and open covalent displacement complex hybridized to analyte, of the present invention. Example 14 shows a first attempt to apply this technique to the solid phase result of the present capturing and immobilizing (separating) steps (as in Example 8, above).

Preparation of Materials Used In Examples 11 and 12 Construction of RM11

Two synthetic oligonucleotides were prepared:

```
RM16     5' CGAAGCTTGGATCCGC 3'
33/SPLINT 3' GCTTCGAACCTAGGCGCTAGGCAGCTGGACGTC 5'
```

10 pmoles of each oligo were mixed in 25 μl of 0.2M Nacl-20 mM Tris-HCl, pH7.5-10mM MgCl$_2$, heated at 80° C. for 5 minutes and allowed to cool slowly to room temperature. The volume was adjusted to 50 μl and 1 mM of each of the four deoxynucleotide triphosphates. 8 units of the Klenow fragment of DNA polymerase I was added and the reaction was incubated at 22° C. for 30 minutes. The blunted 33 mer was then extracted with phenol/chloroform, ethanol precipitated, resuspended and ligated into the M13 vector mpll/SmaI. Phage that had correctly incorporated the blunted 33 mer were identified by hybridization to th RM16 32-P labeled oligonucleotide and confirmed by DNA sequence analysis.

Preparation of biotinylated, labeled DNA

A biotinylated, 32-P labeled DNA was prepared by primer extension off an M13 template using a biotinylated oligonucleotide as primer. Following extension, the sample was digested with a restriction endonuclease and the unique labeled primer extension product was gel purified.

Reaction conditions:

1 μg RM11 template DNA 5 pmole Acyl biotinylated 16-mer (see U.S. Ser. No. 729,700 of Brown, et al, Example VIIA), for this reagent)

Buffer—0.2M NaCl-20 mM Tris-HCl, pH7.5-10mM MgC12

0.5 mM each dCTP, dGTP, TTP 0.5 uM dATP (unlabeled)

25 uCi dATP(-8 pmoles)

Add 4 units Klenow, incubate for 15 minutes at room temperature. Add dATP to final concentration of 0.5 mM. Continue incubation for 15 minutes at RT. Heat kill, 68° C. for 10 minutes. Add 50 μl of 50 mM NaCl-10 mM Tris-HCl, pH7.5-6 mM MgCl$_2$. Add 20 units AvaII and incubate at 37° C. for 1.5 hr. Remove unincorporated deoxynucleotide triphosphates on a G-50 spin column. Add 1/10 volume 1N NaOH and denature for 10 minutes at 65° C. Load on a 1.5% alkaline agarose gel (50 mM NaOH-10 mM EDTA) and elute —225 nt fragment using NA45 paper. The recovered labeled 225-mer is called in Examples 11 and 12 the biotinylated, labeled 225-mer.

Example 11

In the following experiment, the biotinylated, labeled 225-mer was bound to avidin in solution, at room temperature. Buffer or excess free biotin was then added and the samples were incubated at 65° C. for various periods of time. At each timepoint, the sample was rapidly chilled to 4° C. At the completion of the experiment, all samples were electrophoresed on a 5% acrylamide gel (non-denaturing). When the bromophenol blue dye is run 10 cm into gel, the biotinylated, labeled 225-mer separates well (1 cm) from the same biotinylated, labeled 225-mer bound to avidin. At time −0, all the biotinylated, labeled 225-mer was bound to avidin. In the absence of free biotin at 65° C., there was no change in the mobility of the biotinylated, labeled 225-mer at all time points (5, 10, 30, 60, 120 minutes) indicating that under these conditions, no separation of biotin from avidin could be demonstrated. The same result was observed if excess free biotin was added to the samples at the time of chilling to 4° C. However, when free biotin was present during the incubation at 65° C., after 5 minutes at 65° C., more than 80% of the biotinylated, labeled 225-mer migrated at the position of DNA not bound to avidin; after 10 minutes, more than 95% of the biotinylated, labeled 225-mer had been released from the avidin and by 30 minutes, no biotinylated, labeled 225-mer still bound to avidin could be detected. This result indicates that free excess biotin can effectively displace biotinylated DNA from an avidin-DNA complex [in solution]. Control experiments demonstrated that:

1. Addition of excess free biotin to the avidin before labeled DNA was added completely blocked the avidin-DNA interaction;

2. Addition of free biotin to the avidin-DNA complex and incubation at room temperature (22° C.) for 10 minutes resulted in partial displacement (10%);

Example 12—Quantitative displacement kinetics

Streptavidin-agarose (BRL) or streptavidin-latex (Pandex Laboratories) were washed 4× with BB+ (0.2M NaCl, 10 mM Tris-HCl, pH 8.0, 0.01% NP-40) and then resuspended in 1 ml of BB+. To each sample was added approximately 40,000 cpm of labeled, biotinylated 225-mer as described above. Following binding for 10 minutes at room temperature, the agarose or latex bound DNA was separated from unbound DNA by centrifugation and washing in BB+. The washes included 3 room temperature washes and two washes for 10 minutes each at 65° C. Approximately 75% of the counts bound to the support under these conditions. Each avidin support-DNA complex was then aliquoted into 9 equal reactions and either 800 μl BB (without NP40) or 800 μlBB (without NP-40) containing 1 mM free biotin were added to each tube. Following mixing, the samples were placed at 65° C. for 1, 3, 10, or 30 minutes. At each time point, the sample was removed from the 65° C. bath, centrifuged immediately to separate the support from the solution and the supernatant was removed. The pellet was washed twice more with 1 ml BB+ and the supernatants were combined. The agarose or latex pellet was then resuspended in 3 ml BB+ and the pellets and combined supernatants were then counted by Cherenkov counting. The percent of displaced counts (supernatant/[supernatant+pellet]) was then determined for each time point and is presented in Table 5. Similar experiments were also carried out involving displacemnts at 45° C. and 22° C. for longer periods of time (2, 10, 28.5, 45 and 150 minutes). A plot of −1n (1 fraction released) vs time allowed calculations of the relative rates of displacement by free biotin at each of the indicated temperatures:

Relative rates
65° C. 88
5° C. 15–22
22° C. 1

TABLE 6

| Support | Temperature | Time | +/−Biotin | % displacement |
|---|---|---|---|---|
| Agarose | 65 | 1' | − | 1 |
| " | | 3' | − | 1 |
| " | | 10' | − | 0.5 |
| " | | 30' | − | 0.5 |
| Agarose | 65 | 1' | + | 12 |
| " | | 3' | + | 34 |
| " | | 10' | + | 75 |
| " | | 30' | + | 85 |
| Agarose | 22 | 30' | + | 1 |
| Latex | 65 | 1' | − | 4.5 |
| " | | 3' | − | 3.3 |
| " | | 10' | − | 8.1 |
| " | | 30' | − | 12 |
| Latex | 65 | 1' | + | 10 |
| " | | 3' | + | 22 |
| " | | 10' | + | 64 |
| " | | 30' | + | 81 |
| Latex | 22 | 30' | − | 0.8 |
| Agarose | 22 | 2' | + | 5 |
| " | | 10' | + | 6 |
| " | | 28.5 | + | 8 |
| " | | 45' | + | 10 |
| " | | 150' | + | 19 |
| " | | 150' | − | 0.5 |
| Agarose | 45 | 2' | + | 12 |
| " | | 10' | + | 31 |
| " | | 28.5' | + | 50 |
| " | | 45' | + | 50 |
| " | | 150' | + | 70 |
| " | 22 | 150' | − | 1.9 |

Example 13—Background reduction using biotin displacement

Probe preparation

M13 DNA (1 μg) was annealed to the M13 Hybridization probe primer (New England Biolabs, 50 pmoles) and extended as described above except that the final reaction volume was 20 μl and included 16 pmoles 32-P-dATP (3000 Ci/mmole) and 48 pmoles unlabeled dATP and the synthesized DNA was not digested with a restriction endonuclease before G-50 spin column chromatography. Approximately $80 \times 10^6$ cpm were synthesized.

200 μl of avidin agarose from BRL was washed in BB+ and transferred to a small disposable column with a filter containing pores small enough to not permit the agarose beads to flow through. $80 \times 10^6$ cpm of the labeled probe were then passed through this column and reloaded twice. The eluate was collected. The column was then washed twice at room temperature with 5 ml BB+ and the washes were collected. The column was then washed successively with 5 ml of BB+ at 65° C., for approximately 3 minutes each wash. Each wash was collected separately. After 7 washes, 5 ml of BB+ was added and the elution continued for 5 minutes. This sample was then collected and 5 ml of BB+ including 1 mM free biotin was added and the incubation continued for an additional 5 minutes. The counts which are eluted during the plus or minus biotin elutions represent the background which could be expected using this approach. Shown in Table 7 are the expected background as a function of the wash. The expected background is defined as the percentage of input counts that are associated with the pellet after each wash step (for 65° C. washes 1–7) and are calculated by adding counts associated with the pellet at the end of the experiment to the combined preceeding washes. For example for wash 5 the background is:

---
the counts in the final pellet
+ the counts in the 5 minute + biotin elution
+ the counts in the 5 minute − biotin elution
+ the counts in wash 7
+ the counts in wash 6.
---

The expected background for the− biotin and+ biotin washes is defined as the percentage of input counts that were eluted during each− or + biotin elution period. The total counts recovered in the experiment were $79 \times 10^6$ cpm.

TABLE 7

| Wash | Background |
|---|---|
| 0 | 0.0169% |
| 1 | 0.00747% |
| 2 | 0.00502% |
| 3 | 0.00428% |
| 4 | 0.00392% |
| 5 | 0.00350% |
| 6 | 0.00336% |
| 7 | 0.00314% |
| −biotin | 0.000229% |
| +biotin | 0.000235% |

Example 14—Strand displacement, capturing and biotin displacement

In this experiment, the non-covalent p66d Bam HI/EcoRI cut displacement complex described in Example 8 was used. Hae III cut mpll.AllAlb DNA was used as the analyte. A capturer which has a single biotin at the 5' end was synthesized by primer extension of a 5' biotinylated M13 sequencing primer (biotinylated according to the method described in U.S.S.N. 729,700 of Brown, et al.) hybridized to mp19.AlbTaqPst as follows: 20 μg of mp19.AlbTaqPst template, and 20 pm of biotinylated primer in 100 μl of 50 mM NaCl, 10 mM Tris HCl, pH8.0, 10 mM MgCl$_2$ were boiled for 1' in a water bath and allowed to cool to room temperature for 30' in the bath. 3 μl of 5 mM dGTP, dCTP, dATP, dTTp and 2 μl of Klenow fragment Pol I were added, and the reaction incubated 30 minutes at room temperature. A second 1 μl aliquot of Klenow was added and the reaction incubated for 30 additional minutes. The DNA was then digested with Hind III for 2 hours at 37 C to cut out the 300 base primer extended fragment which is complementary to the insert in mp19.Alb-TaqPst. The DNA was denatured by adding 2 μl of 5M NaOH and incubating it for 10' at 65° C. The primer extended fragment was purified after separation by electrophoresis on a 1% alkaline agarose gel with NA45 paper (Schleicher and Schuell). DNA yield was estimated by comparision of an aliquot of the capturer with standards on an ethidium stained gel.

Three reactions were set up as shown in Table 8. Reactions 1 and 2 were incubated for 60 minutes in 50 μl hybridization buffer at 65° C. (reaction 3 was not incubated). 5 μl of reactions 1 and 2 were then removed for gel analysis. The rest of reactions 1 and 2, and reaction 3 were then bound as described in Example 8 to approximately 200 μl packed volume streptavidin agarose. In order to try and minimize sample agitation during the rinses, which may be responsible for a portion of the captured DNA separating from the support in earlier experiments, the samples were rinsed by adding 1 ml of binding buffer to the pellet in an eppendorf tube, inverting the tube five times, and centrifuging it for 3 minutes. Five rinses were done at room temperature, and a final rinse was done at 65° C. for 30 minutes with no shaking after the initial 5 inversions. All supernatents and the final pellet were counted. The results are shown in Table 8. As seen by these data, this gentler washing protocol, or the use of this new smaller and singly biotinylated capturer seems to promote more stable binding of the captured complex to the support. By cutting out and counting the appropriate bands from the gel analysis, it appears that approximately 36% of the captured complexes resolve to form capture-signal strand hybrids, while 64% are apparently present as analyte-complex-capturer intermediates under these reaction conditions.

TABLE 8

| REACTION | pm COMPLEX | pm ANALYTE | pm CAPTURER |
|---|---|---|---|
| 1 | 0.2 noncovalent | 0.2 | 0.5 |
| 2 | 0.2 noncovalent | 0 | 0.5 |
| 3 | 0.2 noncovalent | 0 | 0 |

| | CPM BOUND TO SUPPORT | | |
|---|---|---|---|
| REACTION: | 1 | 2 | 3 |
| TOTAL: | 25623 | 25524 | 29269 |
| RINSE 1: | 13618 | 2884 | 4802 |
| RINSE 2: | 12214 | 723 | 1927 |
| RINSE 3: | 11966 | 519 | 1511 |
| RINSE 4: | 11822 | 454 | 954 |
| RINSE 5: | 11693 | 391 | 845 |
| FINAL | 11174 | 233 | 687 |
| % BOUND: | 43.6% | 0.9% | 2.3% |

Biotin dislacement of captured displaced strands

Reaction 1 to 3 as described above were used. Each sample was the final avidin-agarose pellet after the 30 minute, 60° C. wash described above. One ml BB containing 0.1% NP-40 (BB+) was added to each pellet at room temperature, shaken briefly by inversion and centrifuged to separate the phases (RT wash). One ml BB+ (at 65° C.) was then added and the samples were incubated for 5 minutes at 65° C. The samples were then centrifuged to separate the phases and washed twice with one ml BB+ at room temperature. The combined supernatant phases were then pooled (65° C./5'/-bio). The -biotin, 65° C. wash was repeated once more for sample 3 only. One ml of BB+ containing 1 mM biotin was then added to all samples and these were incubated for 5 minutes, centrifuged and washed as above (65° C./5'/+bio). The final pellet was resuspended in 3 ml BB+ and all samples were counted by Cherenkov counting. Table 9 presents the number of counts and the percentage (in parenthesis) of total counts recovered where applicable in each sample after the background (30 cpm) was subtracted.

TABLE 9

| TREATMENT | 1% | 2% | 3% |
|---|---|---|---|
| RT Wash | 42 | 2 | 57 |
| 65° C./5'/−bio | 182 | 16 | 103 |
| 65° C./5'/−bio | — | — | — |

TABLE 9-continued

| TREATMENT | 1% | 2% | 3% |
|---|---|---|---|
| 65° C./5'/+bio | 7088 (84%) | 70 (54%) | 48 (6%) |
| Pellet | 1151 | 42 | 516 |
| Total | 8463 | 130 | 778 |

The signal to noise ratio before the biotin displacement can be defined as the ratio of counts in the reaction 1 pellet/reaction 2 pellet=48:1 (11174/233). The improvement brought about by the biotin displacement can be measured by the ratio of % counts released by biotin in reaction 1 over the percent counts released by biotin in either reaction 2 or 3. Thus by comparision with reaction 2 the improvement is 0.84/0.54=1.55×. For reaction 3 the improvement is 0.84/0.06=14×. The poor improvement seen in the reaction 2 sample is likely due to the fact that the reaction 2 capturer contains a small amount of M13 polylinker sequence which does result in some capturing by the biotnylated capturer in the absence of analyte. This capturing, though small, would lead to counts released by biotin. The reaction 3 sample (complex only) represents the type of background most likely to be found in an actual displacement measurement and therefore gives a better representation of the background improvement expected.

Example 15—Separation of free signal strands from bound signal strands by capture with a complementary oligomer—5'-GATCATGGCGAC-CACACCCGTCCTGTG (hereafter referred to as anti-27mer).

A 27-base oligomer (5'-CACAG-GACGGGTGTGGTCGCCATGATC, here called 27mer) was extended at its 3' end with biotin-11-dUTP (BRL) using terminal deoxynucleotidyltransferase (IBI). 86% of the molecules were tailed with at least 2 biotinylated nucleotides. No purification of this product was performed. The complement of this oligomer was labeled with gamma 32PATP at its 5' end to a specific activity of $1.7 \times 10^7$ cpm/ug. Hybridization of equimolar amounts of these sequences resulted in the incorporation of all labeled 27mer into duplex DNA (data not shown). In a series of reactions, a constant amount (0.2pmol) of labeled anti27mer was hybridized with varying amounts of cold 27mer for 30 minutes under conditions of 50° C., 8.3 mM Tris, pH 8.1, 0.83 mM EDTA, 166 mM NaCl in a total volume of 12 µl. This produces a series of samples which mimic, inversely, varying amounts of displaced signal strand. Then an excess (0.4pmol) of biotinylated 27mer was added and the hybridization continued for 30 minutes. Half of the resulting sample was then applied in a small volume of 2xSSC, 0.1%SDS to avidin-agarose (Sigma) columns made in siliconized pipet tips with 80 µl slurry. Unbound label was eluted with 900 µl of the same buffer. The amount of radioactivity in each column and eluate was determined. The other half of each hybridization mixture was subjected to electrophoresis on 15% polyacrylamide gels (350V, 2h). Bands corresponding to free anti-27mer and anti-27mer hybridized with biotinylated 27mer were identified through autoradiography. Both separation systems can be used to quantitiate labeled anti-27mer which is hybridized with biotinylated DNA, and thus serve as detection methods for captured displaced signal strands.

Results (Table 10) for avidin columns indicate that as the amount of displacement decreases (mimicked by increasing amounts of unlabeled 27mer), more of the labeled signal strand is excluded from the column. Autoradiography of the polyacrylamide gels shows that as less displacement occurs, the proportion of counts which migrate as double-stranded 27mer increases, while that migrating as duplexes with bio-27mer decreases. Therefore, the exclusion of signal strand from the avidin columns is due to the presence of cold 27-mer hybridized to signal strand, sequestering it from later hybridization with bio-27mer, and from the ensuing avidin separation.

TABLE 10

| Avidin Columns | |
|---|---|
| pmol cold 27 mer | % of total retained |
| 0 | 84 |
| 0.01 | 85 |
| 0.02 | 73 |
| 0.04 | 58 |
| 0.06 | 48 |
| 0.1 | 14 |
| 0.2 | 8 |

Example 16

In order to show that displacement of signal strands from DNA of large size and complex sequence may be monitored by strand capture with biotinylated molecules on avidin columns and to allow simpler quantitation of gel separation, experiments similar to that described in Example 15 were performed. Labeled anti-27mer (0.2pmol, specific activity $1.2 \times 10^7$ cpm/µg) was hybridized with varying amounts of single-stranded M13 mp8 or M13 mp8-20 (thus mimicking inversely varying amounts of displacement), and then subsequently to 0.4 pmol biotinylated 27mer. The 27mer and anti-27mer oligomers are identical in sequence to pBR322, positions 349–375. M13mp8 contains no sequences homologous to the anti-27mer. M13 mp8-20 is a derivative of mp8 into which has been cloned the 1.1kb PstI-BamHI fragment of pBR322, in an orientation such that the + strand is complementary to the anti-27mer (or homologous to the 27mer). Half of each sample was then applied to avidin columns (see Example 16), and the resulting fractions counted. The remaining half was subjected to electrophoresis (350 V, 2h) on 15% polyacrylamide gels. Bands corresponding to M13/anti-27mer hybrid (upper) and bio-27mer/anti-27mer hybrid (lower) were located by autoradiography, excised and counted. Results (Table 11) indicate that gels are as amenable to strand separation as avidin columns.

TABLE 11

| | gel | | avidin columns | |
|---|---|---|---|---|
| pmol M13[1] mp8-20 | cpm lower band | % total hybrid[2] | cpm retained | % total retained[3] |
| 0 | 2305 | 95 | 4309 | 84 |
| 0.1 | 1802 | 49 | 3936 | 60 |
| 0.2 | 425 | 10 | 234 | 6 |
| 0.4 | 450 | 9 | 523 | 9 |
| 0.8 | 357 | 9 | 542 | 9 |
| 1.0 | 329 | 7 | 341 | 7 |
| 2.0 | 219 | 7 | 214 | 7 |

TABLE 11-continued

| pmol M13[1] mp8-20 | gel | | avidin columns | |
|---|---|---|---|---|
| | cpm lower band | % total hybrid[2] | cpm retained | % total retained[3] |
| 3.0 | 264 | 6 | 243 | 6 |

[1] Amounts are an estimate based on O.D. Measurements (as are all the DNAs described), but it is known that the single-stranded DNA preparation contains other nucleic acid contaminants. This amount was added to the entire reaction, of which one half was applied to avidin columns, and the other half to polyacrylamide gels.
[2] cpm in lower band/(cpm in upper and lower bands)
[3] cpm retained/(cpm eluted and cpm in column) The appropriateness of Examples 15 and 16 applying to the capture of displaced labeled polynucleotides can be appreciated by considering that P32-labeled 27-mer(or poly A-tailed 27-mer) (or a variant thereof with a single mismatch) was displaced from M13 strands (or portions thereof) containing the anti-27 mer sequence in the following Examples of the following copending applications:
U.S.S.N. 607,885 of Diamond, et al: 27-mer: 3
mismatched 27-mer: 1, 2, 3, 8, 11, 12
U.S.S.N. 684,308 of Williams, et al. 27-mer: 1-7
U.S.S.N. 684,305 of Collins, et al. 27-mer: 5-14
mismatched 27-mer: 14
U.S.S.N. 729,501 of Unger, et al. 27-mer: 1, 3
enzyme-labeled 27-mer: 2
polyA-tailed 27-mer: 4
U.S.S.N. 729,503 of Vary, et al. polyA-tailed 27-mer: 1, 2

What is claimed is:

1. A method for determining the presence or amount of a predetermined target nucleotide sequence in the nucleic acid of a biological sample which comprises the steps:
    (a) providing a reagent complex of (i) a probe polynucleotide which is capable of binding by complementary base pair binding to the target nucleotide sequence, and (ii) a labeled polynucleotide which is bound by complementary base pair binding to the probe polynucleotide in a first region of the probe polynucleotide at least partially coextensive with the region in which the probe polynucleotide is capable of binding to the target nucleotide sequence;
    (b) contacting the reagent complex with a sample and with a capturing polynucleotide under conditions in which the target nucleotide sequence, if present, binds to the probe polynucleotide and displaces labeled polynucleotide from the reagent complex, and in which the capturing polynucleotide binds by complementary base pair binding selectively to the displaced labeled polynucleotide, in a region of the labeled polynucleotide that had been bound to the probe polynucleotide by complementary base pair binding.
    (c) separating displaced labeled polynucleotide which has bound to capturing polynucleotide from labeled polynucleotide which has not bound to capturing polynucleotide and
    (d) detecting displaced labeled polynucleotide which has bound to capturing polynucleotide and has been separated; and
    (e) relating detection step (d) to determining the presence of said target nucleotide sequence in the nucleic acid of a biological sample.

2. The method of claim 1 wherein the region of the labeled polynucleotide to which the capture polynucleotide binds is a subset of the first binding region which had been bound to the probe polynucleotide and is smaller than the first binding region.

3. The method of claim 1 wherein the capture polynucleotide is immobilizable.

4. The method of claim 3 wherein the capture polynucleotide contains an affinity moiety and the separating step (c) comprises immobilizing capture polynucleotide with any attached labeled polynucleotide onto an immobilized affinity reagent for the affinity moiety.

5. The method of claim 4 wherein the affinity moiety is biotin.

6. The method of claim 4 wherein said affinity reagent is immobilized onto a solid phase.

7. The method of claim 6 wherein the labeled polynucleotide captured onto the affinity reagent is detected on the solid phase.

8. The method of claim 4 wherein the labeled polynucleotide captured onto the immobilized affinity reagent is released into a liquid phase before being detected.

9. The method of claim 8 wherein the displaced labeled polynucleotide is released by dissociating the affinity moiety from the affinity reagent.

10. The method of claim 8 wherein the displaced labeled polynucleotide is released by dissociating displaced labeled polynucleotide from capturing polynucleotide.

11. The method of claim 8 wherein the displaced labeled polynucleotide is released by being redisplaced from the immobilized capture polynucleotide by contact with a selected polynucleotide having a segment complementary to the capture polynucleotide or to the labeled polynucleotide.

12. The method of claim 3 wherein the capture polynucleotide is admixed with reaction mixture after the sample has been incubated with the reagent complex.

13. The method of claim 1 wherein the capture polynucleotide is immobilized.

14. The method of claim 13 wherein the capture polynucleotide is admixed with the reaction mixture after the sample has been incubated with the reagent complex.

15. The method of claim 1 wherein the probe polynucleotide of the reagent complex is immobilized.

16. The method of claim 15 wherein the capture polynucleotide is immobilized.

17. The method of claim 1 wherein the reagent complex is provided in solution.

18. The method of claim 17 wherein the probe polynucleotide is immobilizable and wherein, after the contacting step (b), and before the separating step (c), the probe polynucleotide is immobilized together with undisplaced labeled polynucleotide attached to the probe polynucleotide.

19. The method of claim 17 wherein the capture polynucleotide is immobilizable and, during or after the contacting step (b), capture polynucleotide together with any bound displaced labeled polynucleotide are immobilized.

20. The method of claim 19 wherein the capture polynucleotide is immobilized after the contacting step (b).

21. The method of claim 19 wherein the contacting step (b) comprises simultaneously contacting reagent complex with sample and capture polynucleotide, and wherein the labeled polynucleotide has a first binding region bound in the reagent complex to probe polynucleotide, and wherein the capture polynucleotide has a second binding region capable of binding to a segment of labeled polynucleotide which segment is a subset of the first binding region.

22. The method of claim 19 wherein the contacting step (b) comprises first contacting reagent complex with sample and then, after a hybridization period, contacting the reaction mixture with capture polynucleotide.

23. The method of claim 1 wherein the sample is simultaneously contacted with capture polynucleotide and reagent complex.

24. The method of claim 1 wherein the labeled polynucleotide and probe polynucleotide are joined by a linkage stable to the hybridization and capture conditions.

25. The method of claim 1 wherein the probe polynucleotide and labeled polynucleotide are each sgments of a anode polynucleotide strand.

26. The method of claim 1 wherein the capturing polynucleotide comprises a chemically synthesized oligonucleotide.

27. The method of claim 26 wherein the capturing polynucleotide contains biotin.

28. A kit for determining the presence of a predetermined target nucleotide sequence in the nucleic acid of a biological sample which comprises:
(a) a reagent complex of:
  (i) a probe polynucleotide which is capable of binding by complementary base pair binding to the target nucleotide sequence, and
  (ii) a labeled polynucleotide which is bound by complementary base pair binding of a first binding region of the labeled polynucleotide to a labeled polynucleotide binding region of the probe polynucleotide, which is at least partially coextensive with the region in which the probe polynucleotide is capable of binding to the target nucleotide sequence;
(b) a capture polynucleotide having a second binding region capable of complementary base pair binding selectively to a segment of displaced labeled polynucleotide substantially within the first binding region, and
(c) means for separating the capture polynucleotide together with any bound displaced labeled polynucleotide, from intact reagent complex.

29. The kit of claim 28 wherein the capture polynucleotide is immobilized

30. The kit of claim 28 wherein the capture polynucleotide is immobilizable.

31. The kit of claim 28 wherein the segment is a subset of the first binding region and is smaller than the first binding region.

32. The kit of claim 28 wherein the labeled polynucleotide and probe polynucleotide are joined by a linkage stable to the hybridization and capture conditions.

33. The kit of claim 32 wherein the linkage is a phosphodiester linkage.

34. The kit of claim 28 wherein the probe polynucleotide of the reagent complex is immobilized.

35. The kit of claim 28 wherein the reagent complex is provided in solution or soluble form.

36. The kit of claim 28 wherein the capture polynucleotide comprises a chemically synthesized oligonucleotide.

37. A method for determining the presence of a predetermined target nucleotide sequence in the nucleic acid of a biological sample which comprises the steps:

(a) providing a reagent complex construct which comprises (1) a polynucleotide having: (i) a target binding region segment which is capable of complementary base pair binding to the target nucleotide sequence and (ii) a pairing segment which is bound by complementary base pair binding to a portion of the target binding region segment, and (2) a detectable tag which is in or adjacent to the target binding region segment;
(b) contacting the sample with the reagent complex construct and with a capture polynucleotide under conditions in which the target nucleotide sequence displaces pairing segment from target binding region segment, and in which the capture polynucleotide binds by complementary base pair binding selectively to the displaced pairing segment;
(c) separating polynucleotides which have bound to capture polynucleotide from polynucleotides which have not bound to capture polynucleotide; and
(d) detecting the detectable tag which is on polynucleotides which have bound to capture polynucleotide and have been separated; and
(e) relating detection step (d) to determining the presence of said target nucleotide sequence in the nucleic acid of a biological sample.

38. The method of claim 37 wherein the capture polynucleotide is immobilizable.

39. The method of claim 37 wherein the capture polynucleotide is immobilized.

40. The method of claim 37 wherein a set of nucleotides of the polynucleotide strand which are capable of binding to the capture polynucleotide are a subset of and lesser than the nucleotides of the pairing segment.

41. The method of claim 40 wherein the set of nucleotides is located intermediately within the pairing segment.

42. A kit for determining the presence of a predetermined target nucleotide sequence in the nucleic acid of a biological sample which comprises:
(a) a reagent complex construct which comprises (1) a polynucleotide having: (i) a target binding region segment which is capable of complementary base pair binding to the target nucleotide sequence and (ii) a pairing segment which is bound by complementary base pair binding to a portion of the target binding region segment, and (2) a detectable tag adjacent to the target binding region segment;
(b) a capture polynucleotide capable of complementary base pair binding to the pairing segment selectively when the pairing, segment is displaced from the target binding region segment; and
(c) means for separating capture polynucleotide, together with attached polynucleotide strand, from reagent complex constructs in which the pairing segment remains bound by complementary base pair binding to the target binding region segment.

43. The kit of claim 42 wherein the capture polynucleotide contains an affinity moiety, and wherein the means for separating (c) comprises an immobilized affinity reagent for the affinity moiety.

* * * * *